(12) United States Patent
Chalfie et al.

(10) Patent No.: US 6,319,708 B1
(45) Date of Patent: Nov. 20, 2001

(54) METHOD FOR INCREASING LIFE-SPAN

(75) Inventors: Martin Chalfie, New York, NY (US); James J. Taub, Neptune, NJ (US); Jonathan Rothblatt; Charles Ma, both of New York, NY (US); Jang-Hee Hahn, Chunchon (KR)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 08/980,241

(22) Filed: Nov. 28, 1997

(51) Int. Cl.$^7$ .............................. C12N 15/53; C12N 9/08; A61K 48/00

(52) U.S. Cl. ............... 435/325; 536/23.2; 435/320.1; 435/252.3; 435/192; 435/348; 435/419; 435/254.2; 424/94.4; 514/44

(58) Field of Search ................. 536/23.2; 435/320.1, 435/252.3, 325, 192, 348, 419, 254.2; 424/94.4; 514/44

(56) References Cited

PUBLICATIONS

R. Weiser et al. "Heat Shock Factor–Independent Heat Control of Transcription of the CTT1 Gene Encoding the Cytosolic Catalase T of *Saccharomyces cerevisiae*", J. Biol. Chem. 266(19): 12406–12411, Jul. 1991.*

S.M. Brown et al. "Cloning and Characterization of the katB Gene of Pseudomonas aeruginosaEncoding a Hydrogen Peroxide–Inducible Catalase", J. Bacteriol. 177(22): 6536–6544, Nov. 1995.*

P.E. Perdue et al. "Targeting of Human Catalse to Peroxisomes is Dependent Upon a Novel COOH–Terminal Targeting Sequence", J. Cell Biol. 134(4): 849–862, Jul. 1991.*

Riddle, D. L., *A Genetic Pathway For Dauer Larva Formation In C. elegans, Stadler Genetics Symposium* (1977) 9:101–120 (Exhibit B).

Amstad, P., Peskin, A., Shah, G., Mirault, M.E., Moret R., Zbinden I., and Cerutti, P., "The balance between Cu, Zn–superoxide dismutase and catalase affects thesensitivity of mouse epidermal cells to oxidative stress." *Biochem.* (1991) vol. 30, 9305–9313, (Exhibit 1).

Anderson, G. L., "Superoxide dismutase activity in dauerlarvae of *Caenorhabditis elegans*" (Nematoda: Rhabditidae) *Can. J. Zool.* (1982) vol. 60, 288–291, (Exhibit 2).

Friedman, D. B., and Johnson, T. E., "A mutation in the age–1 gene in Caenorhabditis elegans lengthens life and reduces hermaphrodite fertility." (1987) *Genetics* vol. 188, 75–86 (Exhibit 3).

Gerschman, R., Gilbert, D. L., Nye, S., Dwyer, P., and Fenn, W. O., "Oxygen poisoning and X–irradiation: A mechanism in common." (1954) *Science* vol. 119, 623–626, (Exhibit 4).

Gottlieb, S., and Ruvkun, G., "daf–2, daf–16, and daf–23: Genetically interacting genes controlling dauer formation in *Caenorhabditis elegans*." (1994) *Genetics* vol. 137, 107–120, (Exhibit 5).

Harman, D., "Aging: A theory based on free radical and radiation biology." *J. Gerontol.* (1956) 11, 298–300, (Exhibit 6).

Kenyon, C., Change, J., Gensch, E., Rudner, A., and Tabtiang, R., "A C. elegans mutant that lives twice as long as wild type." *Nature* (1993) vol. 336, 461–464; (Exhibit 7).

Kirkwood, T. B. L., and Rose, M. R., "Evolution of senescence: late survival sacrificed for reproduction." *Phil. Trans. R. Soc. Lond. B* (1991) vol. 332, 15–24, (Exhibit 8).

Klass, M. R., "A method for the isolation of longevity mutants in the nematode *Caenorhabditis elegans* and initial results." *Mech. Ageing Dev.* (1983) vol. 22, 279–286, (Exhibit 9).

Klass, M., and Hirsh, D., "Non–ageing developmental variant of *Caenorhabditis elegans*." *Nature* (1976) vol. 260, 523–525, (Exhibit 10).

Larsen, P. "Aging and resistance to oxidative damage in *Caenorhabditis elegans*." *Proc. Natl. Acad. Sci. USA* (1993) vol. 90, 8905–8909, (Exhibit 11).

Larsen, P., Albert, P. S., and Riddle, D. L., "Genes that regulate both development and longevity in *Caenorhabditis elegans*." *Genetics* (1995) vol. 139, 1567–1583, (Exhibit 12).

Loewen, P., "Bacterial catalases", Oxidative Stress and the Molecular Biology of Antioxidant Defenses. *J. G. Scandalios (ed.)*, Cold Spring Harbor Press, Cold Spring Harbor, NY (1997) pp. 273–308, (Exhibit 13).

Malone, E. A., Inoue, T., Thomas, J. H., "Genetic analysis of the roles of daf–23 and age–1 in regulating *Caenorhabditis elegans* dauer formation." *Genetics* (1996) 143, 1193–1205, (Exhibit 14).

(List continued on next page.)

*Primary Examiner*—Rebecca E. Prouty
(74) *Attorney, Agent, or Firm*—John P. White; Cooper & Dunham LLP

(57) ABSTRACT

This invention provides a composition comprising an amount of a polypeptide effective to increase the life-span of cells wherein the polypeptide has the amino acid sequence of a cytosolic catalase and a suitable carrier. This invention also provides an isolated nucleic acid molecule encoding a cytosolic catalase. This invention also provides a host vector system for the production of a polypeptide having the biological activity of catalase which comprises the above-described vectors in a suitable host. This invention also provides a method for prolonging cell life, comprising: (a) linking the above-described nucleic acids to a regulatory element such that the expression of the above-described nucleic acids is under the control of the regulatory element; and (b) introducing the linked nucleic acid into cells for expression of the nucleic acid, thereby prolonging cell life.

16 Claims, 10 Drawing Sheets

OTHER PUBLICATIONS

Morris, J. Z., Tissenbaum, H. A., Ruvkun, G., "A phosphhatidylinositol–3–OH kinase family member regulating longevity and diapause in *Caenorhabditis elegans.*" *Nature* (1996) 382, 536–539, (Exhibit 15).

Orr, W. C. and Sohal, R. S., "The effects of catalase gene over expression on life span and resistance to oxidative stress in transgenic Drosophilamelanogaster." *Arch.Biochem. Biophys.* (1992) 297, 35–41, (Exhibit 16).

Orr, W. C. and Sohal, R. S.," Effects of Cu–Zn superoxide dismutase overexpression on life span and resistance ot oxidative stress in transgenic *Drosophila melanogaster*." *Arch. Biochem. Biophys.* (1993) 301, 34–40, (Exhibit 17).

Orr, W. C. and Sohal, R. S., "Extension of life–span by overexpression of superoxide dismutase and catalase in *Drosophila melanogaster*." *Science* (1994) 263, 1128–1130, (Exhibit 18).

Phillips, J. P., Campbell, S. D., Michaud, D., Charbonneau, M. and Hilliker, A. J., "Null mutation of copper/zinc superoxide dismutase in Drosophila confers hypersensitivity to paraquat and reduced longevity." *Proc. Natl. Acad. Sci USA* (1989) 86, 2761–2765, (Exhibit 19).

Ruis, H., and Koller, F., "Biochemistry, molecular biology, and cell biology of yeast and fungal catalases", Oxidative Stress and the Molecular Biology of Antioxidant Defenses (1997) J. G. Scandalios (ed.), Cold Spring Harbor Press, Cold Spring Harbor, NY, 309–342, (Exhibit 21).

Scandalios, J. G., Guan, L., and Polidoros, A. N., "Catalases in plants: Gene structure, properties, regulation, and expression", *Oxidative Stress and the Molecular Biology of Antioxidant Defenses.* (1997) J. G. Scandalios (ed.), Cold Spring Harbor Press, Cold Spring Harbor, NY, 343–406, (Exhibit 22).

Seto, N. O. L, Hayashi, S., and Tenner, G. M., "Over expression of Cu–Nz superoxide dismutase in Drosophila does not affect life–span." *Proc. Natl. cad. Sci USA*. (1990) 87, 4270–4274, (Exhibit 23).

Sohal, R. S. and Allen, R. G., "Oxidative stress as a causal factor in differentiation and again: a unifying hypothesis." *Exp. Gerontol.* (1990) 25,499–522, (Exhibit 24).

Staveley, B. E., Phillips, J. P. and Hilliker, A. J., "Phenotypic consequences of copper–zinc superoxide dismutase overexpression in *Drosophila melanogaster.*" *Genome* (1990) 33, 867–872, (Exhibit 25).

Thomas, J. H.,, Birnby, D. A., and Vowels, J.J., "Evidence for parallel processing of sensory information controlling dauer formation in *Caenorhabditis elegans*." *Genetics* (1993) 134, 1105–1117, (Exhibit 26).

Vanfleteren, J. R., "Oxidative stress and ageing in *Caenorhabditis elegans*." *Biochem. J.* (1993) 292, 605–608, (Exhibit 27). and.

Vowels, J. J., and Thomas, J. H., "Genetic analysis of Chemosensor control of dauer formation in *Caenorhabditis elegans.*" *Genetics* (1992) 130, 105–123, (Exhibit 28).

* cited by examiner

FIG. 3

```
CTL-1  MPNDPSDNQLKTYKETYPKPQVITTSNGAPIYSKTAVLTAGRRGPMLMQD   50
CTL-2  ..................................................   50

CTL-1  VVYMDEMAHFDRERIPERVVHAKGAGAHGYFEVTHDITKYGKADMFHKVG  100
CTL-2  .............................S..C...I.N...        100

CTL-1  KQTPLLVRFSTVAGESGSADTVRDPRGFSLKFYTEEGNWDLVGNNTPIFF  150
CTL-2  ......I.....G........A......AI....................  150

CTL-1  IRDAIHFPNFIHALKRNPQTHMRDPNALFDFWMNRPESI-QVMFLYSDRG  199
CTL-2  ...P........TQ.......LK...MI....LH...ALH.....F....  200

CTL-1  IPDGFRFMNGYGAHTFKMVNKEGNPIYCKFHFKPAQPSKNLDPTDAGKLA  249
CTL-2  L...Y.H.....S........D.KA..V......T.GV...TVEK..Q..  250

CTL-1  SSDPDYAIRDLFNAIESRNLPEWKMFIQVMTIEQAEKWEFNPFDVTKVWP  299
CTL-2  ......S.........KGDF.V.........F...................  300

CTL-1  HGDYPLIEVAKMLLNRNVKNYFAEVEQAAFCPAHIVPGIEFSPDKMLQGR  349
CTL-2  .........G..V....PR........S.......................  350

CTL-1  IFSYTDTHYHRLGPNYIQLPVNCPYRSRAHTTQRDGAMAYESQGDAPNYF  399
CTL-2  ........F....................N.........DN.QH...F.  400

CTL-1  PNSFRGYRTRDDVKESTFQTTGDVGSLWTGDDHNYEQPRQFWEKVLKEEE  449
CTL-2  ....NYGK...P...DT..PA....DRYES...N..D.........DTGA  500

CTL-1  RDRV-GNLASDLGGCLEEIQNGMVKEFTKVHPDFG---NALRHQLCQKKH  495
CTL-2  .E.MCQ.F.GP..E.HDF.IK..IDH.S.......ARVK..IQKQARSHI  500
```

FIG. 7

```
ORIGIN
        1 aaatgccaaa cgatccatcg gataatcaac tgaaaaccta caaggagacg tatccaaaac
       61 cccaagtgat cacaacttca aatggagctc cgatctactc gaagaccgcc gtgctcaccg
      121 ccggcggcg tggcccaatg ctcatgcaag atgtagttta tatggatgag atggctcatt
      181 tcgatcgtga acgtatcccc gagcgtgtcg ttcatgccaa gggagccgga gcccatggat
      241 acttcgaggt cacccatgac atcaccaagt acggtaaggc cgatatgttc cacaaggtcg
      301 gaaaacagac accacttctc gttcgttttt caacggtcgc tggagaatcg ggatccgctg
      361 atactgtccg cgatccacgt ggattctctc tcaaattcta taccgaggag ggtaactggg
      421 atctggttgg aaataacact ccgatcttct tcattcgtga cgcaatccac tttccgaatt
      481 tcattcatgc cctgaagcgc aatccacaga ctcacatgag ggatccgaat gcgctcttcg
      541 atttctggat gaatcgccct gaatccattc aggtgatgtt cctctactcg gatcgtggaa
      601 ttcctgatgg attccgtttt atgaatggat acggagcgca tactttcaag atggtcaaca
      661 aggagggaaa tccgatttat tgtaaattcc atttcaagcc tgctcaacct tccaagaatc
      721 tcgatccaac tgacgctgga aagctcgcct cttcggatcc agactatgcg atccgcgacc
      781 tgttcaatgc cattgagtca agaaatttac cggaatggaa gatgttcatt caagtgatga
      841 caatcgaaca agctgagaaa tgggagttca atccatttga tgtcactaaa gtttggccac
      901 acggtgatta cccactgatc gaggtcgcca agatgttgct gaacaggaat gtgaagaatt
      961 atttcgctga ggtcgaacaa gccgccttct gcccggccca catcgtccca ggaatcgagt
     1021 tctcgccaga caagatgctc caagggcgta tcttctccta cacggacacg cattaccatc
     1081 gccttggacc aaactacatt cagcttccag tcaactgccc gtaccgctcc cgtgctcata
     1141 ccactcaacg cgatggtgca atggcttatg aaagccaggg agatgcgccg aattacttcc
     1201 cgaacagttt ccgcggatac cgtactcgtg atgatgtgaa ggagtcgaca tttcagacga
     1261 ctggagatgt tggatcgtta tggactggag acgatcacaa ctacgagcag ccacgtcagt
     1321 tctgggagaa agtgctcaag gaggaggaga gagatcggct cgttgggaat ttggctagtg
     1381 atttgggtgg ctgtttggag gaaattcaaa atggaatggt caaagagttc acgaaagttc
     1441 atccggattt cggaaatgct cttcgccatc agctctgcca gaagaagcat taaattgttt
     1501 ga
```

FIG. 8A ctagaaaccaaaATGccaaacgatccatcggataatcaactgaaacctacaaggagacgtatccagtgagtttagagtttaaagg cacagacgcattttctacaacaacaactactatttacagtaacttgtttcagaaacccccaagtgatcacaacttcaaatggagctcctatcta ctcgaagaccgccgtgcgcaccgccgggcgcgtggcccaatgctcatgcaagatgtagtttatatggatgagatggctcatttcgat cgtgaacgtatcccgagcgtgtagttcatgccaagggagccggagcccatggatactcgaggtcacccatgacatcaggaagtact gtaaggccgatatgttcaacaaggtcggaaaacagacaccactctcgttcgttttcaacggtcgctggagaatcgggatccgctg atactgtccgcgatccacgtggattctctctcaaattctataccgaggagggtaactgggatctggttggaataacactccgatctt cttcattcgtgacgcaatccacttccgaatttcattcatgccctgaagcgcaatccacacactcacatgagggatccgaatgcgctctt cgatttctggatcaatcgccctgaatccattcatcaggtgtagttcctctactcggatcgtggaattcctgatggattccgttttatgaat ggatacggagcgcatactttcaagatggtcaacaaggaggaaatccgatttattgtaaattccatttcaaggtaagcctaagagag acggggactagaattaaattttcattttctattttcagcctgctcaaggttccaaagaatctcgatccaacctgacgctggaagctcgctct cctcggatccagactatgcgatccgccgacctgttcaatgccattgagtcaagaaatttcccggaatggaagatgttcattcaagtgat gacattcgaacaagctgagaaatgggagttcaatccatttgatgtcactaaagtttggccacacggtgattacccactgatcgaggt cggcaagatggtgctgaacaggaatgtgaagaattatttcgctgaggcaagtggtgtgaagatgaattagtttttttaatattaggtctcc aaataagttccgggtcaaaaatcataactttgttcgctgtgtatcgattttatgaaactgtaggaatttacgttatcaactatgatctttcatttgaca atagtcacaaaattttttggccgtccgaagtgccctaactcggagccaattttttcaggcattttcagatctcgcttctttcaggtttcaattgagg tttgtgtgcggattttgcttagtttagtacacaatgtaagaaaacaaaaagtttggaaaaaatccgtccaaaaaaatttttttgtcggtcgtcaaaa aatcttcaaaaaattttttcgaaaattctcgatttttatacaaaaatgatgtaaccatgtgcaaactatttacacatacaaaacatttcaatttattgc gtcacactaaaacaataacagaaaacacagcttttcgaaaaattttcgagttcttggagtatttctcgagatccaaatttcatactcaaatgttttg tatgtgtaaaaatagtttgcacatggttacatcattcttgtaataaaaaatcgagaattttcgaaaaaaaattttttttgaagattttttgacgaccgac aaaaaaaattttttggacggattttttccaaactttttgttttcttacattgtgtactaaactaagcaaaatccgcacacaaacctcaattgaaacctg aaaagaagcgagatctgaaaaatgcctgaaaaaaatggctccgagttagggcgctccgggtggtcaaaaaatttgtgaccatttcaaaatg aaaggtcatagttgataacataaattcccaaagtttcaaaaaaatctataaaaggcaaaaaaagttctgattttgacccgggaacttatttggga gacctaataggaacaataaaaattgcattttacgtctagctttaaaggtggagtaaaaatattttttattttggtttcaggtcgaacaagccgcct tctgccnggcccgtcccaggaatcgagttctcgccagacaagatgctccaaggcgtatcttctcctacacggacacgcattaccat cgccttggaccaaactacattcagcttccagtcaactgcccgtaccgctcccgtgctcataccactcaacgcgatggtgcaatggctt atgaaagccaggggagatgcgccgaattacttcccgaacagtttccgcgggataccgtactcgtgatgatgtgaaggagtcgacatt tcagacgactggagatgttgatcgttatgagactggagacgatcacaactacgagcagccacgtcagttctgggagaaagtgctca

FIG. 8B aggaggaggagagagatcggctcgttgggaatttggctagtgatttgggtggctgtttggaggaaattcaaatggatgtcaagagt cacgaagtcatccggattttcggaaatgctcttcgccatcagctctgccggaagaagcatTAAattgtttgatattcaaactttttgat atatgaactctgttatttataaactcttttttttgtatttcttctggttttgatgataagaaatttatgtgcacataaatcaaaaagccggaaattaa tagcgtttatcaggcagaaaattggccacgtgacgtcatcatttcctgtttgaagaaaatctggaaaattttttgtttcagtcaattttttaaagatga aaacttaagttagactgtaaaagcaattttcgcgccaaaattacggtatcgggtctcgaaacgacagttttttatctattgcgaaaatatgtgctc ctttaaagagtactgtgttgcaaactttttgtcgctgtggagttttttatcgattttttatattttttcgatgagaacaactcaaatataacaataaaaac acaaaattaaaaaanaaaatcgatnaaaaaatccgcgtcaacgaaagtttaaagttacagtatttgtcgtttcgagaccgggtaccg tagtttttggtgaaaacattgcaaaatttggtcaacaatttcatcgctgcgagaccgacacaacactttattttattttgggtttcccttatcgc ttatcataaacatgtgacgtcatcatctcttgtgcaccgcgactgggagtataagaatcgccggaaaacatcaataatcagttcggtagaagt gaaaattgagcgtaaatatgatcatttttcgatgcaccatatttgacgcgcaatacttctacaagccgctgtgtactgctcgtggacaactttgga ttattttttgttttaaaattcaaaatagtcaatatattgcttatttatagcgcgccttttttgacagtaagtttgtcaaatttgcgcgtaagttatggtgttt gcacatatgcaccatacagcaacaccccgcggcccggctagtggtacatccatgcaaatgcgctctactgataattgagttaacaggttagg cgcaagataagaaaagctttggaccaaaaaatttagagtttattttttttcggacatttttatatacatcacaaaaatattgggccactcgttttgat aaaaacgacaagcccaaaagttcaggtatacggtagacaaattgcgyacaggtaccacttttttccacgtaggccaggttgtcccattacgctt tgatctatgaaaaatgcgggaattttttcgtccagaaaatgtgacgtcagcacgttctcaaccatgcgaaatcagttgaaaactctgcgtctattc tcccgncattttttntgtnagatctgtagatttgtagatcaatccattccccgtatacccctgacccataatcaatacctacctaattttttgtctttc cccctacttttttgcctgtccaaaataagcgagactatgccgtagtctgngtgtccaacaacatgttccttatcagtgataacgctacaatct tctttcttttttctctgtttctcttgtctctcccaacccatattccgtattacacctcgtcgtggtcattttttttgttca gagttttatttaattctaaatttcctaactaaaaaaccaaaATGccaaacgatccatcggataatcaactgaaaacctacaaggagacg tatccagtgagtttagagtctaaaggcacagacgcatttttctacaacaacaactactatttacagtaacttgtttcagaaacccaagtgatca caacttcaatggagctccgatctactcgaagaccgccgtgctcaccgccggcggcgtggnnccncaatgctcatgcaagatgtag tttatatggatgagatggctcatttcgatcgtgaacgtatccccgagcgtgtcgttcatgccaaggggagccggagcccatggatactt cgaggtcacccatcacatctccaagtactgtaaggccgatatcttcaacaaggtcgggaagcagacccactgctaattagattctct acagtcggtggtgagagcgtaccgccgacaccgctcgtcatccacgtggatttgcgatcaagttctacaccgaggagggaaactgg gatctggttggaaataacactccgatattcttcatcngtgaccctatccacttccgaactttatcataccagaagcgtaatccacaga ctcacctgaaggatccaacatgatcttgacttctggattcatagaccagaggctttgcatcaagtgatgttcctgttttccgatcgagg nctcccagatgggtaccgtcatgtgaatggatacggatcccatacattcaagatggttaacaaggacggaaagctatctatgtga

FIG. 8C aattccatttcaaggtgggtccttaatgttatttaaattttcggtctataatttccaacttcag<u>ccaactcaaggagtgaagaatctcaccgtg</u>

<u>gagaaggccggtcaacttgcctcttcggacccagactatcatccgtgacctgttcaatgctattgagaggagacttcagtatggaag</u>

<u>agttcattcaagtgatgacattcgacagctgagaaatgggagttcaatccatttgatgtcactaaagtttggccacacggtgattacc</u>

<u>cactgatcgaggtcggcaagatggtgctgaacagaaatccaaggaactacttcgctgagg</u>taatgggctgggcttgaccgcctagtt gcgcgctaaggtggcctagtcggtcccttttctactcggactgtttctataccggagagcttttgcggtacggtagtctcgtaggattgtgtttg gtactgtacagagccaaagttttttggggttaccacagaaagagagcaggttcttctcattcaccacaactattactattcgagtcagggtggta cagaagctaggtgagtgcaaacgtgctctaccgaacgagtaaattttcttgcggccattttcatatgcatcgcaaaatccaaatttgggttagt tttcgagatagcagccaatacaggttttttagactgattatcatgaaccaagccatctagtttctgtgctaccgtgtgaagtgtggtaaggcatgc aattgcgctctaacgagaaactagggccccataagacggaattgatagctctcacgtggtgccagactgtcccattatggtttgttttttttatca acaaaaaatgcgggaatttttttgcacaaaaaatgagacttcagcagttcttaaccatgcgaaatcagttgaaaaccttgcgtctcttctccccg catttttttttgtagatcaaagtagatcaagccgaaatgagacactctgacaccacgtgagttcaacgtgaatagctagtttgggaaacacaaa aacgttttccaaaactacagtaatcctacagtactttatttccaggt<u>tgaacaatccgccttctgcccgcccacatcgtcccaggaatcga</u>

<u>agttctcgccacacaagatgctccaaaggacgtatcttctcgtacaccgacactcatttccaccgccttggaccaaactacatccagc</u>

<u>ttccagtcaactgcccgtaccgctcccgtgctcataacacccagcgtgatggtgcaatggctatgacaatcagcaacatgctccaaa</u>

<u>cttccttcccgaacagcttcaactatggaagactcgtccggatgtcaaggataccacattcccagccactggagatgtttgatcgtta</u>

<u>tgaaagtggagatgacaacaaactatgatcaacccgtcaattctgggagaaggttttggataccggggctcgggagagaatgtgc</u>

<u>cagaactttgcagggccgctcggggaatgtcatgatttcattattaagggaatgatcgatcacttttcagaggttcatccagattttggagc</u>

<u>tcgtgtcaaggcactcatccagaaacaggctcgctctcatatcTAAactttcttgaaattaaaagaaattaaatgtacttttattgtaata</u>

<u>acttgctttattgtgtataaaaaatatgataattaaaagtaaataaagttaatataaacttaaactctccaccaactcacagcggatgtaaa</u>

<u>gctctaaacttatcagcaagcctctggcccaacagcgagtcatgcttcagggtctccctctccaccagcagctcaggcgtcaaagccca</u>

<u>attcttgggatccttgctcagaatgcaagactgtatcagtgtctgaac</u>

SEQUENCE LISTING

<160> NUMBER OF SEQ ID NOS: 8

<210> SEQ ID NO 1
<211> LENGTH: 27
<212> TYPE: DNA
<213> ORGANISM: Nematodes

<400> SEQUENCE: 1
cgctctagaa accaaaatgc caaacga                                    27

<210> SEQ ID NO 2
<211> LENGTH: 22
<212> TYPE: DNA
<213> ORGANISM: Nematodes

<400> SEQUENCE: 2
ctcgaagtat ccatgggctc cg                                         22

<210> SEQ ID NO 3
<211> LENGTH: 41
<212> TYPE: DNA
<213> ORGANISM: Nematodes

<400> SEQUENCE: 3
ggcgctagca acaaaaatga gtaaaggaga agaactttt c                     41

<210> SEQ ID NO 4
<211> LENGTH: 32
<212> TYPE: DNA
<213> ORGANISM: Nematodes

<400> SEQUENCE: 4
gcctctagaa tctgcttgct agctttgtat ag                              32

<210> SEQ ID NO 5
<211> LENGTH: 495
<212> TYPE: PRT
<213> ORGANISM: Nematodes

<400> SEQUENCE: 5

Met Pro Asn Asp Pro Ser Asp Asn Gln Leu Lys Thr Tyr Lys Glu Thr
 1               5                  10                  15

Tyr Pro Lys Pro Gln Val Ile Thr Thr Ser Asn Gly Ala Pro Ile Tyr
                20                  25                  30

Ser Lys Thr Ala Val Leu Thr Ala Gly Arg Arg Gly Pro Met Leu Met
            35                  40                  45

Gln Asp Val Val Tyr Met Asp Glu Met Ala His Phe Asp Arg Glu Arg

```
              50                  55                  60
Ile Pro Glu Arg Val Val His Ala Lys Gly Ala Gly Ala His Gly Tyr
 65                  70                  75                  80
Phe Glu Val Thr His Asp Ile Thr Lys Tyr Gly Lys Ala Asp Met Phe
                 85                  90                  95
His Lys Val Gly Lys Gln Thr Pro Leu Leu Val Arg Phe Ser Thr Val
                100                 105                 110
Ala Gly Glu Ser Gly Ser Ala Asp Thr Val Arg Asp Pro Arg Gly Phe
                115                 120                 125
Ser Leu Lys Phe Tyr Thr Glu Gly Asn Trp Asp Leu Val Gly Asn
                130                 135                 140
Asn Thr Pro Ile Phe Ile Arg Asp Ala Ile His Phe Pro Asn Phe
145                 150                 155                 160
Ile His Ala Leu Lys Arg Asn Pro Gln Thr His Met Arg Asp Pro Asn
                165                 170                 175
Ala Leu Phe Asp Phe Trp Met Asn Arg Pro Glu Ser Ile Gln Val Met
                180                 185                 190
Phe Leu Tyr Ser Asp Arg Gly Ile Pro Asp Gly Phe Arg Phe Met Asn
                195                 200                 205
Gly Tyr Gly Ala His Thr Phe Lys Met Val Asn Lys Glu Gly Asn Pro
                210                 215                 220
Ile Tyr Cys Lys Phe His Phe Lys Pro Ala Gln Pro Ser Lys Asn Leu
225                 230                 235                 240
Asp Pro Thr Asp Ala Gly Lys Leu Ala Ser Asp Pro Asp Tyr Ala
                245                 250                 255
Ile Arg Asp Leu Phe Asn Ala Ile Glu Ser Arg Asn Leu Pro Glu Trp
                260                 265                 270
Lys Met Phe Ile Gln Val Met Thr Ile Glu Gln Ala Glu Lys Trp Glu
                275                 280                 285
Phe Asn Pro Phe Asp Val Thr Lys Val Trp Pro His Gly Asp Tyr Pro
290                 295                 300
Leu Ile Glu Val Ala Lys Met Leu Leu Asn Arg Asn Val Lys Asn Tyr
305                 310                 315                 320
Phe Ala Glu Val Glu Gln Ala Ala Phe Cys Pro Ala His Ile Val Pro
                325                 330                 335
Gly Ile Glu Phe Ser Pro Asp Lys Met Leu Gln Gly Arg Ile Phe Ser
                340                 345                 350
Tyr Thr Asp Thr His Tyr His Arg Leu Gly Pro Asn Tyr Ile Gln Leu
                355                 360                 365
Pro Val Asn Cys Pro Tyr Arg Ser Arg Ala His Thr Thr Gln Arg Asp
                370                 375                 380
Gly Ala Met Ala Tyr Glu Ser Gln Gly Asp Ala Pro Asn Tyr Phe Pro
385                 390                 395                 400
Asn Ser Phe Arg Gly Tyr Arg Thr Arg Asp Asp Val Lys Glu Ser Thr
                405                 410                 415
Phe Gln Thr Thr Gly Asp Val Gly Ser Leu Trp Thr Gly Asp Asp His
                420                 425                 430
Asn Tyr Glu Gln Pro Arg Gln Phe Trp Glu Lys Val Leu Lys Glu Glu
                435                 440                 445
Glu Arg Asp Arg Val Gly Asn Leu Ala Ser Asp Leu Gly Gly Cys Leu
                450                 455                 460
Glu Glu Ile Gln Asn Gly Met Val Lys Glu Phe Thr Lys Val His Pro
465                 470                 475                 480
```

Asp Phe Gly Asn Ala Leu Arg His Gln Leu Cys Gln Lys Lys His
               485                 490                 495

<210> SEQ ID NO 6
<211> LENGTH: 107
<212> TYPE: PRT
<213> ORGANISM: Nematodes

<400> SEQUENCE: 6

Ser Cys Ile Asn Ile Gly Ala Ala Ile Pro Thr Gln Leu Lys Met Ile
 1               5                  10                  15

Leu His Ala Leu His Phe Leu Tyr His Ser Asp Lys Ala Val Thr Gly
                20                  25                  30

Val Thr Val Glu Lys Gln Ser Lys Gly Asp Phe Val Phe Gly Val Pro
             35                  40                  45

Arg Ser Phe Asn Asp Asn Gln His Phe Asn Tyr Gly Lys Pro Asp Thr
         50                  55                  60

Pro Ala Asp Arg Tyr Glu Ser Asn Asp Thr Gly Ala Glu Met Cys
 65                  70                  75                  80

Gln Phe Gly Pro Glu His Asp Phe Ile Lys Ile Asp His Ser Ala Arg
                 85                  90                  95

Val Lys Ile Gln Lys Gln Ala Arg Ser His Ile
            100                 105

<210> SEQ ID NO 7
<211> LENGTH: 1502
<212> TYPE: DNA
<213> ORGANISM: Nematodes

<400> SEQUENCE: 7
aaatgccaaa cgatccatcg gataatcaac tgaaaaccta caaggagacg tatccaaaac      60
cccaagtgat cacaacttca aatggagctc cgatctactc gaagaccgcc gtgctcaccg     120
ccgggcggcg tggcccaatg ctcatgcaag atgtagttta tatggatgag atggctcatt     180
tcgatcgtga acgtatcccc gagcgtgtcg ttcatgccaa gggagccgga gcccatggat     240
acttcgaggt cacccatgac atcaccaagt acggtaaggc cgatatgttc acaaggtcg      300
gaaaacagac accacttctc gttcgttttt caacggtcgc tggagaatcg ggatccgctg     360
atactgtccg cgatccacgt ggattctctc tcaaattcta taccgaggag ggtaactggg     420
atctggttgg aaataacact ccgatcttct tcattcgtga cgcaatccac tttccgaatt     480
tcattcatgc cctgaagcgc aatccacaga ctcacatgag ggatccgaat gcgctcttcg     540
atttctggat gaatcgccct gaatccattc aggtgatgtt cctctactcg gatcgtggaa     600
ttcctgatgg attccgtttt atgaatggat acggagcgca actttcaag atggtcaaca     660
aggagggaaa tccgatttat tgtaaattcc atttcaagcc tgctcaacct tccaagaatc     720
tcgatccaac tgacgctgga aagctcgcct cttcggatcc agactatgcg atccgcgacc     780
tgttcaatgc cattgagtca agaaatttac cggaatggaa gatgttcatt caagtgatga     840
caatcgaaca agctgagaaa tgggagttca atccatttga tgtcactaaa gtttggccac     900
acggtgatta cccactgatc gaggtcgcca agatgttgct gaacaggaat gtgaagaatt     960
atttcgctga ggtcgaacaa gccgccttct gcccggccca catcgtccca ggaatcgagt    1020
tctcgccaga caagatgctc caagggcgta tcttctccta cacggacacg cattaccatc    1080
gccttggacc aaaactacat tcagcttcca gtcaactgcc gtaccgctcc cgtgctcata    1140

-continued

```
ccactcaacg cgatggtgca atggcttatg aaagccaggg agatgcgccg aattacttcc    1200
cgaacagttt ccgcggatac cgtactcgtg atgatgtgaa ggagtcgaca tttcagacga    1260
ctggagatgt tggatcgtta tggactggag acgatcacaa ctacgagcag ccacgtcagt    1320
tctgggagaa agtgctcaag gaggaggaga gagatcggct cgttgggaat tggctagtg     1380 atttgggtgg ctgtttggag gaaattcaaa atggaatggt caaagagttc acgaaagttc    1440
atccggattt cggaaatgct cttcgccatc agctctgcca gaagaagcat taaattgttt    1500
ga                                                                   1502
```

<210> SEQ ID NO 8
<211> LENGTH: 6840
<212> TYPE: DNA
<213> ORGANISM: Nematodes
<220> FEATURE:
<221> NAME/KEY: N_region
<222> LOCATION: (2138)
<223> OTHER INFORMATION: N= g, a, c or t(u)
<221> NAME/KEY: N_region
<222> LOCATION: (3054)
<223> OTHER INFORMATION: N= g, a, c or t(u)
<221> NAME/KEY: N_region
<222> LOCATION: (3060)
<223> OTHER INFORMATION: N= g, a, c or t(u)
<221> NAME/KEY: N_region
<222> LOCATION: (3070)
<223> OTHER INFORMATION: N= g, a, c or t(u)
<221> NAME/KEY: N_region
<222> LOCATION: (3905)
<223> OTHER INFORMATION: N= g, a, c or t(u)
<221> NAME/KEY: N_region
<222> LOCATION: (3913)
<223> OTHER INFORMATION: N= g, a, c or t(u)
<221> NAME/KEY: N_region
<222> LOCATION: (3917)
<223> OTHER INFORMATION: N= g, a, c or t(u)
<221> NAME/KEY: N_region
<222> LOCATION: (4045)
<223> OTHER INFORMATION: N= g, a, c or t(u)
<221> NAME/KEY: N_region
<222> LOCATION: (4412)..(4413)
<223> OTHER INFORMATION: N= g, a, c or t(u)
<221> NAME/KEY: N_region
<222> LOCATION: (4416)
<223> OTHER INFORMATION: N= g, a, c or t(u)
<221> NAME/KEY: N_region
<222> LOCATION: (4735)
<223> OTHER INFORMATION: N= g, a, c or t(u)
<221> NAME/KEY: N_region
<222> LOCATION: (4876)
<223> OTHER INFORMATION: N= g, a, c or t(u)

<400> SEQUENCE: 8

```
ctagaaacca aaatgccaaa cgatccatcg gataatcaac tgaaacctac aaggagacgt      60
atccagtgag tttagagttt aaaggcacag acgcattttc tacaacaaca actactattt     120
acagtaactt gtttcagaaa ccccaagtga tcacaacttc aaatggagct cctatctact     180
cgaagaccgc cgtgcgcacc gccgggcgcg tggcccaatg ctcatgcaag atgtagttta     240
tatggatgag atggctcatt tcgatcgtga acgtatcccg agcgtgtagt tcatgccaag     300
ggagccggag cccatggata ctcgaggtca cccatgacat caggaagtac tgtaaggccg     360
atatgttcaa caaggtcgga aaacagacac cacttctcgt tcgtttttca acggtcgctg     420
gagaatcggg atccgctgat actgtccgcg atccacgtgg attctctctc aaattctata     480
ccgaggaggg taactgggga tctggttgga ataacactcc gatcttcttc attcgtgacg     540
caatccactt ccgaatttca ttcatgccct gaagcgcaat ccacacactc acatgaggga     600
```

| | |
|---|---|
| tccgaatgcg ctcttcgatt tctggatcaa tcgccctgaa tccattcatc aggtgtagtt | 660 |
| cctctactcg gatcgtggaa ttcctgatgg attccgtttt atgaatggat acggagcgca | 720 |
| tactttcaag atggtcaaca aggagggaaa tccgatttat tgtaaattcc atttcaaggt | 780 |
| aagcctaaga gagacgggga ctagaattaa attttcattt tctattttc agcctgctca | 840 |
| aggttccaaa gaatctcgat ccaacctgac gctggaagct cgctctcctc ggatccagac | 900 |
| tatgcgatcc gcgacctgtt caatgccatt gagtcaagaa atttcccgga atggaagatg | 960 |
| ttcattcaag tgatgacatt cgaacaagct gagaaatggg agttcaatcc atttgatgtc | 1020 |
| actaaagttt ggccacacgg tgattaccca ctgatcgagg tcggcaagat ggtgctgaac | 1080 |
| aggaatgtga agaattattt cgctgaggca gtggtgtga agatgaatta gttttttta | 1140 |
| atattaggtc tccaaataag ttccgggtca aaatcataa cttttgttcgc tgtgtatcga | 1200 |
| tttttatgaa actgtaggaa tttacgttat caactatgat ctttcatttg acaatagtca | 1260 |
| caaaattttt tggccgtccg aagtgcccta actcggagcc aattttttca ggcatttttc | 1320 |
| agatctcgct tcttttcagg tttcaattga ggtttgtgtg cggattttgc ttagtttagt | 1380 |
| acacaatgta agaaaacaaa aagtttggaa aaaatccgtc caaaaaaatt ttttttgtcg | 1440 |
| gtcgtcaaaa aatcttcaaa aaatttttt cgaaaattct cgatttttat acaaaaatga | 1500 |
| tgtaaccatg tgcaaactat tttacacata caaaacattt caatttattg cgtcacacta | 1560 |
| aaacaataac agaaaacaca gcttttcga aaaattttcg agttcttgga gtatttctcg | 1620 |
| agatccaaat ttcatactca aatgttttgt atgtgtaaaa atagtttgca catggttaca | 1680 |
| tcattcttgt aataaaaaat cgagaattt cgaaaaaaaa ttttttgaa gatttttga | 1740 |
| cgaccgacaa aaaaaatttt tggacggatt ttttccaaac tttttgtttt cttacattgt | 1800 |
| gtactaaact aagcaaaatc cgcacacaaa cctcaattga aacctgaaaa gaagcgagat | 1860 |
| ctgaaaaatg cctgaaaaaa atggctccga gttagggcgc tccgggtggt caaaaaattt | 1920 |
| tgtgaccatt tcaaaatgaa aggtcatagt tgataacata aattcccaaa gtttcaaaaa | 1980 |
| aatctataaa aggcaaaaaa agttctgatt tttgacccgg gaacttattt gggagaccta | 2040 |
| ataggaacaa taaaaattgc attttacgtc tagctttaaa ggtggagtaa aaatattttt | 2100 |
| tattttggtt ttcaggtcga acaagccgcc ttctgccngg cccgtcccag gaatcgagtt | 2160 |
| ctcgccagac aagatgctcc aagggcgtat cttctcctac acggacacgc attaccatcg | 2220 |
| ccttggacca aactacattc agcttccagt caactgcccg taccgctccc gtgctcatac | 2280 |
| cactcaacgc gatggtgcaa tggcttatga agccaggga gatgcgccga attacttccc | 2340 |
| gaacagtttc cgcgggatac cgtactcgtg atgatgtgaa ggagtcgaca tttcagacga | 2400 |
| ctggagatgt tgatcgttat gagactggag acgatcacaa ctacgagcag ccacgtcagt | 2460 |
| tctgggagaa agtgctcaag gaggaggaga gagatcggct cgttgggaat ttggctagtg | 2520 |
| atttgggtgg ctgtttggag gaaattcaaa tggatgtcaa gagtcacgaa gtcatccgga | 2580 |
| ttttcggaaa tgctcttcgc catcagctct gccggaagaa gcattaaatt gtttgatatt | 2640 |
| caaactttg atatatgaac tctgttattt ataaactctt ttttttgtat ttcttctggt | 2700 |
| tttgatgata agaatttat gtgcacataa atcaaaaagc cggaaattaa tagcgttat | 2760 |
| caggcagaaa attggccacg tgacgtcatc attttcctgt ttgaagaaaa tctggaaaat | 2820 |
| ttttttgtttc agtcaatttt taaagatgaa aacttaagtt agactgtaaa agcaattttc | 2880 |
| gcgccaaaat tacggtatcg ggtctcgaaa cgacagtttt ttatctattg cgaaaatatg | 2940 |
| tgctccttta aagagtactg tgttgcaaac ttttgtcgct gtggagtttt tatcgatttt | 3000 |

```
ttatattttt tcgatgagaa caactcaaat ataacaataa aaacacaaaa ttanaaaaan    3060
aaaatcgatn aaaaaatccg cgtcaacgaa agtttaaagt tacagtattt gtcgtttcga    3120
gaccgggtac cgtagttttt ggtgaaaaca ttgcaaaatt tggtcaacaa tttcatcgct    3180
gcgagaccga cacaacactt tattttattt ttgggtttcc cttatcgctt atcataaaca    3240
tgtgacgtca tcatctcttg tgcaccgcga ctgggagtat aagaatcgcc ggaaaacatc    3300
aataatcagt tcggtagaag tgaaaattga gcgtaaatat gatcattttt cgatgcacca    3360
tatttgacgc gcaatacttc tacaagccgc tgtgtactgc tcgtggacaa ctttggatta    3420
ttttttgttt ttaaaattca aaatagtcaa tatattgctt atttatagcg cgcctttttg    3480
acagtaagtt tgtcaaattt gcgcgtaagt tatggtgttt gcacatatgc accatacagc    3540
aacaccccgc ggcccggcta gtggtacatc catgcaaatg cgctctactg ataattgagt    3600
taacaggtta ggcgcaagat aagaaaagct ttggaccaaa aaatttagag tttattttt    3660 tcggacatt tttatataca tcacaaaaat attgggccac tcgttttga taaaaacgac    3720 aagcccaaaa gttcaggtat acgtagaca aattgcgyac aggtaccact ttttccacgt    3780
aggccaggtt gtcccattac gctttgatct atgaaaaatg cgggaatttt tcgtccagaa    3840
aatgtgacgt cagcacgttc tcaaccatgc gaaatcagtt gaaaactctg cgtctattct    3900
cccgncattt ttntgtnaga tctgtagatt tgtagatcaa tccattcccc gtataccctg    3960
acccataatc aataccctacc taattttgt cttttccccct actttttgc ctgtccaaaa    4020 taagcgagac tatgccgtag tctgngtgtc caacaacatg ttccttatca gtgataacgc    4080
tacaatcttt tttctttttt ctctgtttct cttgtctctc ccaacccata ttccgtatta    4140
cacctcgtcg tggtcatttt tttgttcaga gttttattta attctaaatt tcctaactaa    4200
aaaaccaaaa tgccaaacga tccatcggat aatcaactga aaacctacaa ggagacgtat    4260
ccagtgagtt tagagtctaa aggcacagac gcattttcta caacaacaac tactatttac    4320
agtaacttgt ttcagaaacc ccaagtgatc acaacttcaa tggagctccg atctactcga    4380
agaccgccgt gctcaccgcc gggcggcgtg gnnccncaat gctcatgcaa gatgtagttt    4440
atatggatga gatggctcat ttcgatcgtg aacgtatccc cgagcgtgtc gttcatgcca    4500
agggagccgg agcccatgga tacttcgagg tcacccatca catctccaag tactgtaagg    4560
ccgatatctt caacaaggtc gggaagcaga cccactgcta attagattct ctacagtcgg    4620
tggtgagagc gtaccgccga caccgctcgt catccacgtg gatttgcgat caagttctac    4680
accgaggagg gaaactggga tctggttgga aataacactc cgatattctt catcngtgac    4740
cctatccact tccgaacttt atcataccag aagcgtaatc cacagactca cctgaaggat    4800
ccaacatgat cttgacttct ggattcatag accagaggct ttgcatcaag tgatgttcct    4860
gttttccgat cgaggnctcc cagatgggta ccgtcatatg aatggatacg gatcccatac    4920
attcaagatg gttaacaagg acggaaaggc tatctatgtg aaattccatt tcaaggtggg    4980
tccttaatgt tatttaaatt tttcggtcta taatttccaa cttcagccaa ctcaaggagt    5040
gaagaatctc accgtggaga aggccggtca acttgcctct tcggacccag actatcatcc    5100
gtgacctgtt caatgctatt gagaggagac ttcagtatgg aagagttcat tcaagtgatg    5160
acattcgaca gctgagaaat gggagttcaa tccatttgat gtcactaaag tttggccaca    5220
cggtgattac ccactgatcg aggtcggcaa gatggtgctg aacagaaatc caaggaacta    5280
cttcgctgag gtaatgggct gggcttgacc gcctagttgc gcgctaaggt ggcctagtcg    5340
```

-continued

```
gtcccttttc tactcggact gtttctatac cggagagctt ttgcggtacg gtagtctcgt    5400
aggattgtgt tttggtactg tacagagcca aagtttttg gggttaccac agaaagagag    5460
caggttcttc tcattcacca caactattac tattcgagtc agggtggtac agaagctagg    5520
tgagtgcaaa cgtgctctac cagaacgagt aaattttct tgcggccatt ttcatatgca    5580
tcgcaaaatc caaattttgg gttagttttc gagatagcag ccaatacagg tttttagact    5640
gattatcatg aaccaagcca tctagtttct gtgctaccgt gtgaagtgtg gtaaggcatg    5700
caattgcgct ctaacgagaa actagggccc cataagacgg aattgatagc tctcacgtgg    5760
tgccagactg tcccattatg gtttgttttt tttatcaaca aaaaatgcgg gaattttttt    5820
gcacaaaaaa tgagacttca gcagttctta accatgcgaa atcagttgaa aaccttgcgt    5880
ctctttctcc ccgcattttt ttttgtagat caaagtagat caagccgaaa tgagacactc    5940
tgacaccacg tgagttcaac gtgaatagct agtttgggaa acacaaaaac gttttccaa    6000 aactacagta atcctacagt actttatttc caggttgaac aatccgcctt ctgcccggcc    6060
cacatcgtcc caggaatcga agttctcgcc acacaagatg ctccaaagga cgtatcttct    6120
cgtacaccga cactcatttc caccgccttg gaccaaacta catccagctt ccagtcaact    6180
gcccgtaccg ctcccgtgct ataacaccca gcgtgatggt gcaatggcta tgacaatcag    6240
caacatgctc caaacttcct tcccgaacag cttcaactat ggaagactcg tccggatgtc    6300
aaggatacca cattcccagc cactggagat gtttgatcgt tatgaaagtg gagatgacaa    6360
caaactatga tcaaccccgt caattctggg agaaggtttt ggataccggg gctcgggaga    6420
gaatgtgcca gaactttgca gggccgctcg gggaatgtca tgatttcatt attaagggaa    6480
tgatcgatca cttttcaaag gttcatccag attttggagc tcgtgtcaag gcactcatcc    6540
agaaacaggc tcgctctcat atctaaactt tcttgaaatt aaaagaaatt aaatgtactt    6600
tttattgtaa taacttgctt tattgtgtat aaaaaatatg ataattaaaa ataaataaag    6660
ttaatataac ttaaactctc caccaactca cagcggatgt aaagctctaa acttatcagc    6720
aagcctctgg cccaacagcg agtcatgctt cagggtctcc ctctccacca gcagctcagg    6780
cgtcaaagcc caattcttgg gatccttgct cagaatgcaa gactgtatca gtgtctgaac    6840
```

METHOD FOR INCREASING LIFE-SPAN

The invention disclosed herein was made with Government support under NIH Grants No. GM30997 and AG14461 from the Department of Health and Human Services. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains.

BACKGROUND OF THE INVENTION

C. elegans and other nematodes can halt development under appropriate conditions (overcrowding, reduction in food supply) by becoming a nonfeeding stage (an alternative third larval stage) called the dauer larva. This stage is similar to the dispersal stage of many parasitic nematodes (Roberts and Janovy, Jr., 1996). C. elegans dauers can exist for extended periods (at least two months) without effects on subsequent post-dauer life-span or progeny production (Klass and Hirsh, 1976).

Several genes affect the transition into and out of the dauer state (Riddle et al., 1981). These dauer formation (daf) genes can be mutated to cause animals to always (the Daf-C, dauer constitutive, phenotype) or never (the Daf-D, dauer defective, phenotype) form dauer larvae. Most researchers agree that two interlinked genetic pathways control dauer formation (Vowels and Thomas, 1992; Thomas et al., 1993; Gottlieb and Ruvkun, 1994; Larsen et al., 1995).

Recent work has implicated one of these pathways in the control of aging. Specifically, Kenyon et al. (1993) showed that a daf-c mutation in the daf-2 gene caused a doubling of life-span in C. elegans. This increase was suppressed by a daf-d mutation in the daf-16 gene. Larsen et al. (1995) extended these observations, finding that daf-c mutations in daf-2 and daf-23 extended life-span. This extension of life-span was suppressed completely by mutations in daf-16 and partially by mutations in daf-18. These workers also found that certain daf-2; daf-12 double mutants had greatly extended life-spans, even though daf-12 mutations on their own did not affect aging.

These results place the most famous C. elegans aging gene, age-1, in a broader context. An age-1 mutation was identified by Klass (1983) and studied by Friedman and Johnson (1987), who showed that it extended both average and maximum life-span in C. elegans. The age-1 mutation is now known to be an allele of daf-23 (Malone et al., 1996). Moreover, Morris et al. (1996) have found that daf-23 encodes a subunit of a PI 3-kinase, indicating a role of signaling in determinating life-span.

The dauer pathway, when expressed in adults, allows animals to survive for relatively long periods of time (at least a four-fold extension in mean life-span). The targets of the dauer pathway genes that allow life-span extension, however, have not been identified, previously. Some of the ultimate targets for the daf genes may be genes encoding antioxidant enzymes, since catalase and superoxide dismutase (SOD) activities are approximately five times higher in the dauer larvae than in L3 worms (Anderson, 1982; Larsen, 1993). Moreover, unlike the activities in wild-type animals, total SOD and catalase activities increase with age in age-1 mutants (Vanfleteren, 1993; Larsen, 1993).

Several investigators have hypothesized that oxidative damage to cells is a major cause of cellular and organismal senescence (Gershmann et al., 1954; Harman, 1956; Sohal and Allen, 1990). Most relevant to our studies are experiments in Drosophila melanogaster where overexpression of Cu/Zn SOD and catalase, but not either alone, increased mean adult life-span by 33% (Seta et al., 1990; Stavely et al., 1990; Orr and Sohal, 1992, 1993, 1994). These results not only suggest that control of reactive oxygen species is an important determinant of longevity, but also underline the need to balance SOD and catalase activities for the control of oxidative stress (see also Phillips et al., 1989 and Amstad et al., 1991).

Here we show that C. elegans contains two catalase genes. One gene, ctl-1, appears to be needed for normal life-span and for the extension of life-span seen in daf-c adults. One striking feature of the ctl-1 catalase is its localization in the cytosol, not in peroxisomes. This localization is unusual, since cytosolic catalases have rarely, if ever, been seen in animals. The second C. elegans catalase gene, ctl-2, appears to encode the peroxisomal catalase. We suggest that the ctl-1 catalase is needed during periods of starvation, such as the dauer larva, and that its expression in daf-c adults enables them to live longer. As such ctl-1 would represent a true life-span extension gene.

In nematodes an alternative third larval stage, often called the dauer stage in free-living animals, allows animals to weather periods of low food availability (if free living) or to disperse (if parasitic). Mutations in several genes that control entry into and exit from the dauer stage of the nematode Caenorhabditis elegans profoundly affect the life-span of adults. The ctl-1 gene, which encodes an unusual, cytosolic catalase, is required in C. elegans for the life-span extension exhibited by animals with these dauer mutations. Cytosolic catalase may have evolved in nematodes to allow prolonged periods of dormancy before reproductive maturity.

SUMMARY OF THE INVENTION

This invention provides a composition comprising an amount of a polypeptide effective to increase the life-span of cells wherein the polypeptide has the amino acid sequence of a cytosolic catalase and a suitable carrier.

This invention also provides a composition comprising an amount of a nucleic acid molecule comprising a nucleotide sequence encoding a cytosolic catalase effective when introduced into cells to produce a sufficient amount of cytosolic catalase to increase the life-span of cells and a suitable carrier.

This invention also provides an isolated nucleic acid molecule encoding a cytosolic catalase.

This invention also provides a host vector system for the production of a polypeptide having the biological activity of catalase which comprises the above-described vectors in a suitable host.

This invention also provides a method for prolonging cell life, comprising: (a) linking the above-described nucleic acids to a regulatory element such that the expression of the above-described nucleic acids is under the control of the regulatory element; and (b) introducing the linked nucleic acid into cells for expression of the nucleic acid, thereby prolonging cell life.

BRIEF DESCRIPTION OF THE FIGURES

FIG. 3 The ctl-1 (SEQ. ID NO. 5) and ctl-2 (SEQ. ID NO. 6). Alignment of ctl-1 and ctl-2 amino acid sequences. The peroxisomal targeting signal is underlined in CTL-2.

FIG. 7 The cDNA sequence of ctl-1 (SEQ. ID NO. 7)

FIG. 8 The genomic sequence of ctl-1 and ctl-2. Exons are in bold underline. Sequence derived from the genome project is in bold italics (SEQ. ID NO. 8)

DETAILED DESCRIPTION OF THE INVENTION

Figure 1:
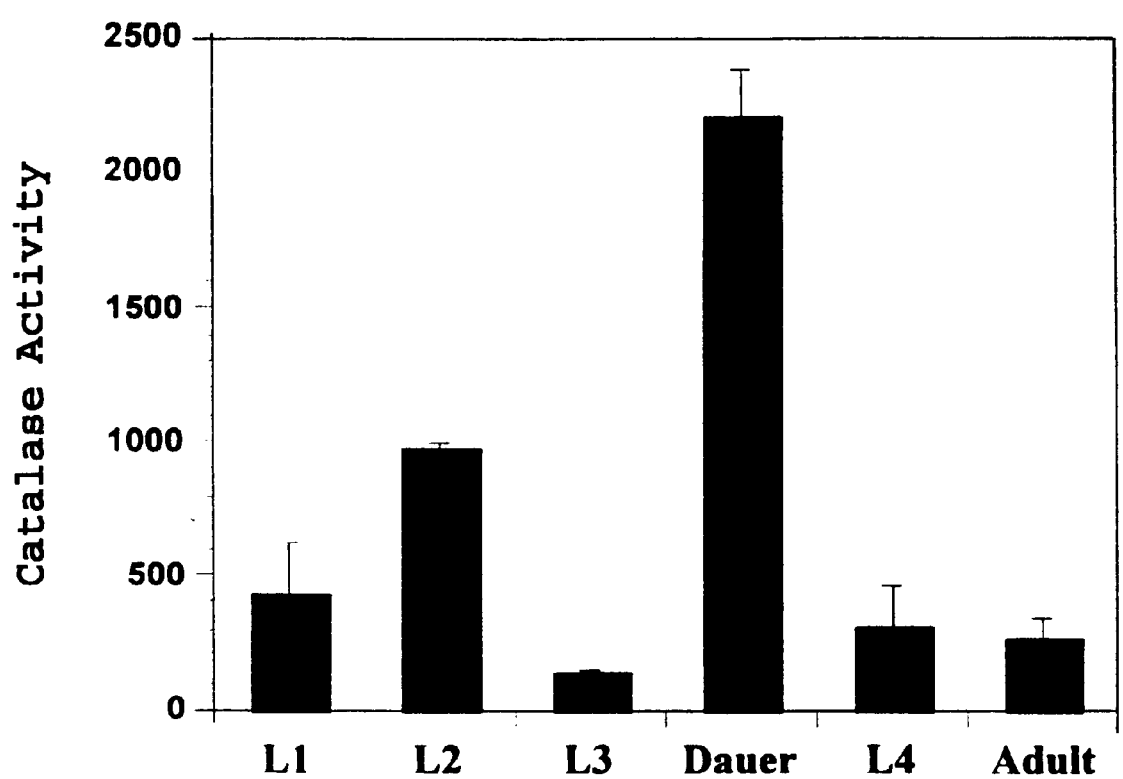
FIG. 1 Catalase activity during C. elegans development. Total (N2) animals is highest in the L2 larval stage and (cytosolic plus peroxisomal) catalase activity in wild-type declines slightly during normal development. Catalase activity is 5-fold higher in the dauer larvae than in other larval stages. Each value is the mean ± SD of three independent experiments.

This invention provides a composition comprising an amount of a polypeptide effective to increase the life-span of cells wherein the polypeptide has the amino acid sequence of a cytosolic catalase and a suitable carrier.

As used herein the effective amount of the polypeptide will be based upon the size of the polypeptide, the biodegradability of the polypeptide, the bioactivity of the polypeptide and the bioavailability of the polypeptide. If the polypeptide does not degrade quickly, is bioavailable and highly active, a smaller amount will be required to be effective. The effective amount will be known to one of skill in the art; it will also be dependent upon the form of the polypeptide, the size of the polypeptide and the bioactivity of the polypeptide. Variants of the catalase with higher activity will require lower dosages than variants of the catalase with lower activity. One of skill in the art could routinely perform empirical activity tests to determine the bioactivity in bioassays and thus determine the effective amount.

Suitable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

As used herein, a cytosolic catalase refers to a catalase that is localized in the cytosol unlike most catalases which are localized in the peroxisomes. Cytosolic catalases lack a peroxisomal targeting signal (PTS).

Also contemplated are animal model systems which elucidate the physiological roles of cytosolic catalase protein and are produced by creating transgenic animals in which the expression of a cytosolic catalase protein is either increased or decreased, or the amino acid sequence of the expressed cytosolic catalase protein is altered by a variety of techniques. Examples of these techniques include, but are not limited to: 1) Insertion of normal or mutant versions of DNA encoding a C. elegans cytosolic catalase or homologous animal versions of these genes, especially a human homolog of the cytosolic catalase gene, by microinjection, retroviral infection or other means well known to those skilled in the art, into appropriate fertilized embryos in order to produce a transgenic animal (Hogan B. et al. Manipulating the Mouse Embryo, A Laboratory Manual, Cold Spring Harbor Laboratory (1986)) or, 2) Homologous recombination (Capecchi M. R. Science 244:1288–1292 (1989); Zimmer, A. and Gruss, P. Nature 338:150–153 (1989)) of mutant or normal, human or animal versions of these genes with the native gene locus in transgenic animals to alter the regulation of expression or the structure of these cytosolic catalase proteins. The technique of homologous recombination is well known in the art. It replaces the native gene with the inserted gene and so is useful for producing an animal that cannot express the native gene encoding the cytosolic catalase protein but does express, for example, an inserted mutant gene encoding a mutant cytosolic catalase protein, which has replaced the native cytosolic catalase gene in the animal's genome by recombination, resulting in underexpression of the cytosolic catalase protein. Microinjection adds genes to the genome, but does not remove them, and so is useful for producing an animal which expresses its own and added cytosolic catalase protein, resulting in overexpression of the cytosolic catalase protein.

One means available for producing a transgenic animal, with a mouse as an example, is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986)). DNA or cDNA encoding a vertebrate cytosolic catalase protein is purified from a vector (such as plasmid pMT21 2hh #7 described above) by methods well known in the art. Inducible promoters may be fused with the coding region of the DNA to provide an experimental means to regulate expression of the trans-gene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a pipet puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only method for inserting DNA into the egg cell, and is used here only for exemplary purposes.

Since the normal action of cytosolic catalase protein-specific drugs is to mimic, activate or inhibit the cytosolic catalase protein, the transgenic animal model systems described above are useful for testing the biological activity of drugs directed to mimic or alter the cytosolic catalase protein activity even before such drugs become available. These animal model systems are useful for predicting or evaluating possible therapeutic applications of drugs which mimic, activate or inhibit the rat cytosolic catalase protein by alleviating abnormalities observed in the transgenic animals associated with decreased or increased expression of the native cytosolic catalase gene or cytosolic catalase trans-gene. Thus, a model system is produced in which the biological activity of drugs specific for the cytosolic catalase protein are evaluated before such drugs become available. The transgenic animals which over or under produce the cytosolic catalase protein indicate by their physiological state whether over or under production of the cytosolic catalase protein is therapeutically useful. It is therefore useful to evaluate drug action based on the transgenic model system. Therefore, an animal which underexpresses cytosolic catalase protein is useful as a test system to investigate whether the actions of a pharmaceutical compound comprising cytosolic catalase is in fact therapeutic. Another use is that if overexpression is found to lead to abnormalities, then a drug which acts as an antagonist to the cytosolic catalase protein is indicated as worth developing, and if a promising therapeutic application is uncovered by these animal model systems, activation or inhibition of the cytosolic catalase protein is achieved therapeutically either by producing agonist or antagonist drugs directed against the vertebrate cytosolic catalase protein or by any method which increases or decreases the activity of the cytosolic catalase protein.

Also contemplated are nucleic acids probes. In an embodiment, the probe is a nucleic acid molecule of at least 15 nucleotides capable of specifically hybridizing with a sequence of a nucleic acid molecule encoding cytosolic catalase can be used as a probe. Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encodes the cytosolic catalase into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the DNA molecule which encodes the cytosolic catalase downstream of a bacteriophage promoter such as T3, T7 or SP6. Large amounts of RNA probe may be produced by incubating the labeled nucleotides with the linearized fragment where it contains an upstream promoter in the presence of the appropriate RNA polymerase.

This invention is broadly applicable to a wide range of species, including mammals. Because of sequence homologies across species, cytosolic catalase genes from animals other than *C. elegans* including mammals and humans may be isolated using probes generated based on the *C. elegans* cytosolic catalase gene. Such screens would focus on the C-terminus of cytosolic catalase since this region differs markedly from that of peroxisomal catalase. For example, such screens could be done on human cDNA libraries via radioactively labeled probes derived from the C-terminal sequence of the *C. elegans* cytosolic catalase gene. Clones that show positive hybridization can be further analyzed by DNA sequencing techniques which are well known to those of ordinary skill in the art.

This invention also provides the above-described composition, further comprising an effective amount of superoxide dismutase.

As used herein the effective amount of the polypeptide will be based upon the size of the polypeptide, the biodegradability of the polypeptide, the bioactivity of the polypeptide and the bioavailability of the polypeptide. If the polypeptide does not degrade quickly, is bioavailable and highly active, a smaller amount will be required to be effective. The effective amount will be known to one of skill in the art; it will also be dependent upon the form of the polypeptide, the size of the polypeptide and the bioactivity of the polypeptide. Variants of the superoxide dismutase (SOD) with higher activity will require lower dosages than variants of SOD with lower activity. One of skill in the art could routinely perform empirical activity tests to determine the bioactivity in bioassays and thus determine the effective amount.

This invention also provides a composition comprising an amount of a nucleic acid molecule comprising a nucleotide sequence encoding a cytosolic catalase effective when introduced into cells to produce a sufficient amount of cytosolic catalase to increase the life-span of cells and a suitable carrier.

This invention also provides the above-described compositions, further comprising an effective amount of superoxide dismutase.

This invention also provides the above-described compositions, wherein the catalase has an amino acid sequence which is identical to or substantially similar to the catalase shown in FIG. 3.

This invention also provides the above-described compositions, wherein the catalase is a peroxisomal catalase from which the peroxisomal signal has been deleted.

The vast majority of catalases present in animals are localized in the peroxisomes as a result of a peroxisomal targeting signal (PTS). Deleting the PTS effectively creates a non-peroxisomal catalase.

This invention also provides a method of increasing the life-span of cells, comprising administering to cells the above-described compositions.

This invention also provides a method of increasing the life-span of cells in a subject, comprising administering to the subject the above-described compositions.

This invention also provides an isolated nucleic acid molecule encoding a cytosolic catalase.

This invention also provides the above-described nucleic acid molecules, wherein the nucleic acid molecule is a DNA molecule.

This invention also provides the above-described nucleic acid molecules, wherein the nucleic acid molecule is a cDNA molecule or a genomic DNA molecule.

This invention also provides the above-described nucleic acid molecules, wherein the nucleotide sequence is set forth in FIG. 7.

This invention also provides the above-described nucleic acid molecules, wherein the nucleotide sequence is the same or substantially the same as shown in FIG. 8.

This invention also provides the above-described nucleic acid molecules, wherein the nucleic acid molecule is an RNA molecule.

This invention also provides the above-described nucleic acid molecules, wherein the nucleic acids molecules code for a cytosolic catalase that has the same or substantially the same amino acid sequence as shown in FIG. 3.

This invention also provides a vector comprising the above-described nucleic acid molecules.

This invention also provides the above-described vectors, wherein the vector is a plasmid.

This invention also provides a host vector system for the production of a polypeptide having the biological activity of catalase which comprises the above-described vectors in a suitable host.

As used herein, the biological activity of catalase includes its activity as an antioxidant. In one mode of antioxidant activity catalase can break down $H_2O_2$ and other peroxides.

This invention also provides the above-described host vector systems, wherein the suitable host is a bacterial cell, yeast cell, insect cell, animal cell or plant cell.

This invention also provides the above-described plasmid designated TU#527.

This plasmid, TU#527 was deposited on Nov. 26, 1997 with the American Type Culture Collection (ATCC), 12301 Parklawn Drive, Rockville, Md. 20852, U.S.A. under the provisions of the Budapest Treaty for the International Recognition of the Deposit of Microorganism for the Purposes of Patent Procedure. The TU#527 was accorded ATCC Accession Number 209503.

This invention also provides a cell comprising the above-described isolated nucleic acids.

This invention also provides a cell comprising the above-described vectors.

This invention also provides a method for prolonging cell life, comprising: (a) linking the above-described nucleic acids to a regulatory element such that the expression of the above-described nucleic acids is under the control of the regulatory element; and (b) introducing the linked nucleic acid into cells for expression of the nucleic acid, thereby prolonging cell life.

This invention also provides the above-described methods, further comprising: linking a nucleic acid encoding a cystolic catalase to a regulatory element such that the expression of the nucleic acid encoding a cystolic catalase is under the control of the regulatory element and introducing the linked nucleic acid encoding a cystolic catalase into the cell.

This invention also provides the above-described methods, wherein the regulatory element is a promoter.

This invention also provides the above-described methods, wherein the promoter is a tissue-specific promoter.

This invention also provides the above-described methods, wherein the promoter is an inducible promoter.

EXPERIMENTAL DETAILS

Experimental Results

Catalase activity is regulated in *C. elegans*. Total catalase activity in wild-type (N2) worms is highest in the early larval stages (L1 and L2) and decreases as worms mature (FIG. 1). Catalase activity is more than five-fold higher in the daf-2 dauer larvae than in normal L3 animals, a result that is similar to that of Vanfleteren (1993). These results suggest an important role for catalase in dauer larvae. Catalase could provide protection from $H_2O_2$ generated as a byproduct of peroxisomal fatty acid β-oxidation or provide a more general antioxidant defense. (No information is available on the level of peroxisomal β-oxidation in dauer larvae.)

Figure 2A:
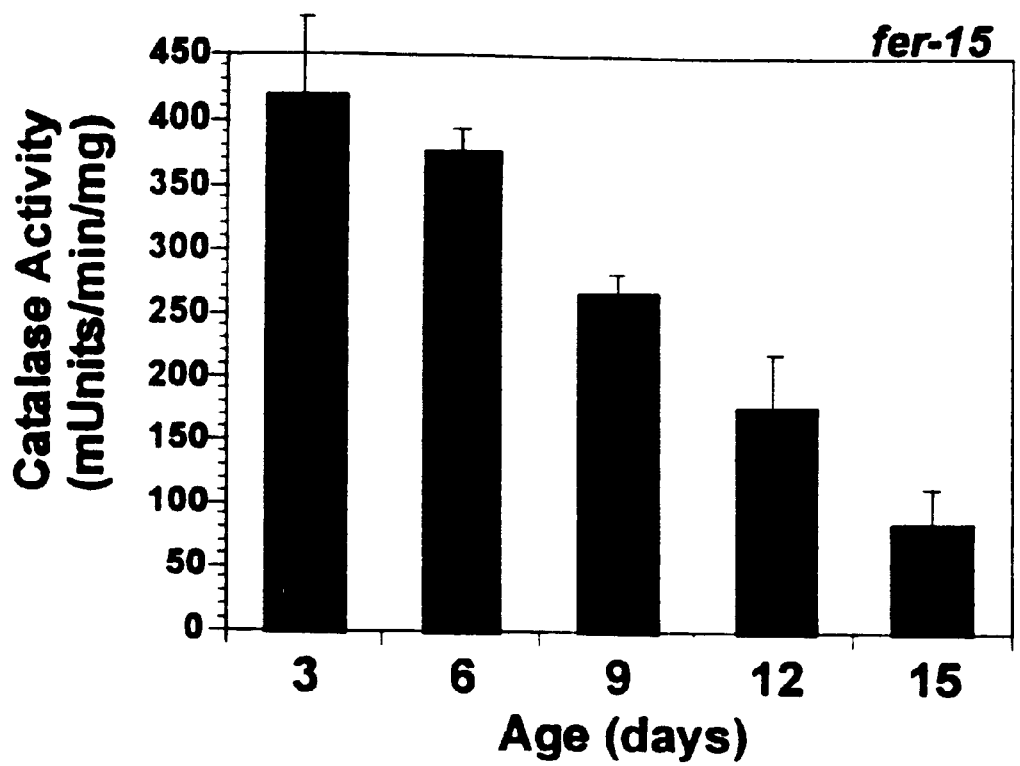
FIGS. 2A and 2 Catalase activity in aging adult C. elegans at 25° C. (A) Catalase activity steadily declines as fer-15 (b26ts) worms age. The decline in catalase activity in these animals mirrors the appearance of signs of aging, such as decreased movement and feeding activity. (B) Catalase activity increases as age-1(hx546) fer-15 (b26ts) worms age. Each value is the mean ± SD of three independent experiments.
Figure 2B:
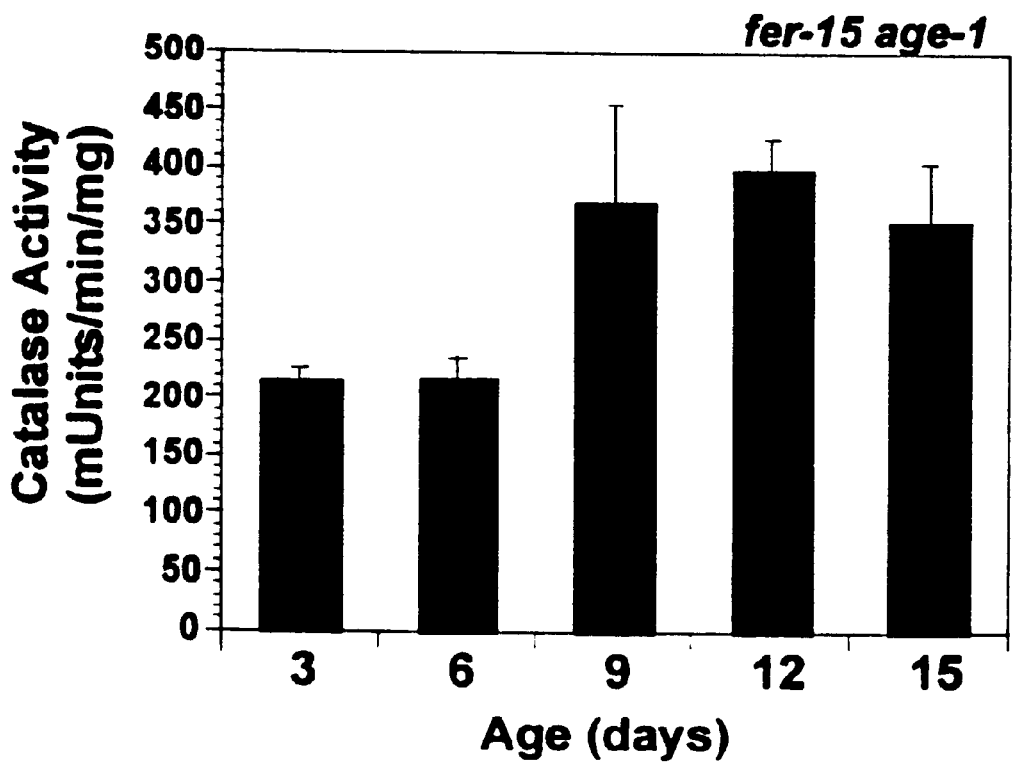

Catalase activity decreases as *C. elegans* adults age, but the decrease is minimized in age-1 animals (FIG. 2). While age-1 animals displayed elevated levels of catalase activity and locomotor activity even very late in life, control animals showed an earlier decline in catalase activity that mirrored the appearance of signs of aging, such as decreased movement and feeding activity.

*C. elegans* contains two catalases. Using a partial *C. elegans* cDNA, cm20b12, that was identified as a catalase cDNA by the *C. elegans* Genome Project (Waterston et al., 1992), we probed a *C. elegans* cDNA library (Barstead and Waterston, 1989) and recovered nineteen cDNAs encoding two catalases, ctl-1 and ctl-2, with different restriction patterns. The ctl-1 cDNA differs from cm20b12, but sequences in the ctl-2 cDNA matched it and a complete cDNA sequence submitted to the EMBL database by K. J. Henkle-Duehrsen (Accession Number X82175). The two catalases share extensive regions of identity at both the nucleotide and amino acid levels (FIG. 3). The CTL-1 and CTL-2 catalases are 82% identical; the region of greatest divergence is the carboxyl terminal 50 amino acids. Although the ctl-1 and ctl-2 cDNAs encode the same first 270 nucleotides of cDNA sequences, the mRNAs do not result from alternative splicing. The genes exist tandemly on chromosome II (FIG. 8B).

Figure 4:
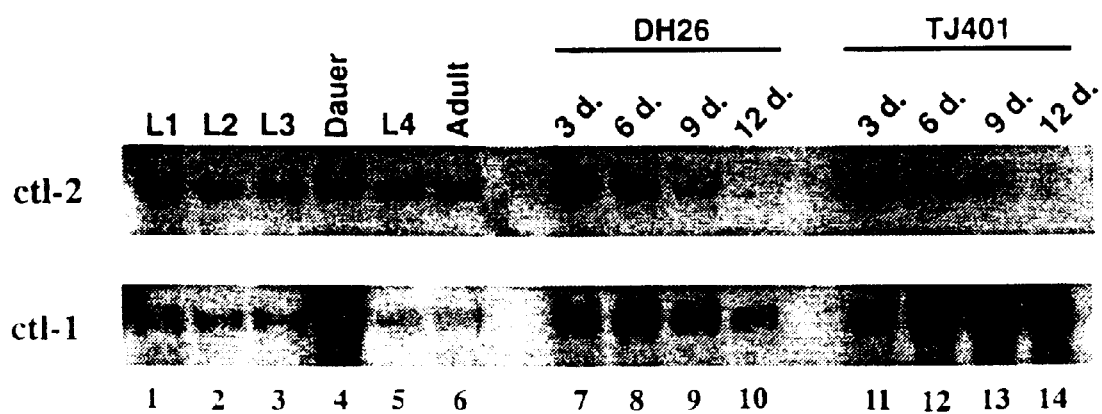
FIG. 4 Abundance of ctl-1 and ctl-2 mRNAs during development and aging of C. elegans. The level of ctl-1 mRNA is highest in dauer larvae and in age-1 worms. The abundance of ctl-2 mRNA remains constant through out early development and declines as the adult animals age. Wild-type N2 animals (lanes 1–3 and 5–6) were harvested at the indicated developmental stages. Dauer larvae (lane 4) were produced by growing daf-2(e1370) animals at the non-permissive temperature of 25° C. DH26 (lanes 7–10) and TJ401 (lanes 11–14) animals were harvested at 3, 6, 9, and 12 days after hatching.

Unlike the CTL-2 protein, which contains a conservative variant of the canonical Type I peroxisomal targeting signal (Gould et al., 1989) at its C-terminus, CTL-1 lacks a peroxisomal targeting signal (FIG. 3). To determine the subcellular localization of the CTL-1 and CTL-2 proteins, we expressed gene fusions in which the gene for the Aequorea victoria green fluorescent protein (gfp) was fused to the 5' end of the entire coding region of ctl-1 or ctl-2 from a heat-shock promoter in Caenorhabditis elegans. As expected, worms expressing the ctl-2gfp fusion displayed a punctate pattern of GFP expression typical of localization to peroxisomes, whereas animals expressing the ctl-1gfp fusion displayed diffuse fluorescence consistent with cytosolic localization (data not shown). Expression of similar constructs in the yeast *Saccharomyces cerevisiae* gave the same results (data not shown).

ctl-1 and ctl-2 mRNAs are differentially regulated. The level of ctl-2 mRNA remains constant in wild-type animals as they develop to adulthood and does not change substantially in daf-2 dauer larvae as compared to wilde-type L3 worms (FIG. 4). With abundant food the level of ctl-1 mRNA decreases slightly as the worms mature. This decrease in ctl-1 mRNA abundance mirrors the decrease in catalase activity measured in developing animals. In contrast to ctl-2, ctl-1 mRNA is markedly increased in dauer larvae. These results suggest that ctl-1 is responsible for the increase in catalase activity detected in dauer larvae.

Figure 5:
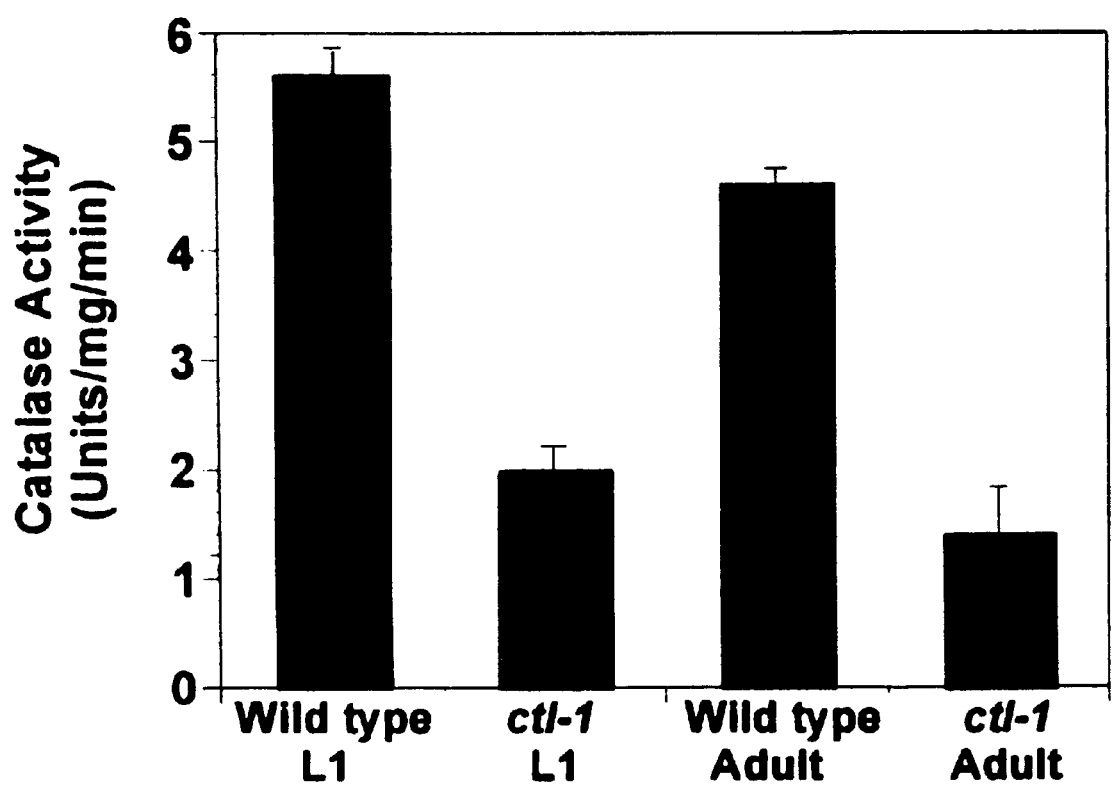
FIG. 5 Catalase activity in N2 and ctl-1 mutant animals. Catalase activity is reduced more than 50% in the ctl-1 mutant when compared to the N2 wild-type strain. Reduced activity is observed in both larval (L1) and adult stages.
Figure 6:
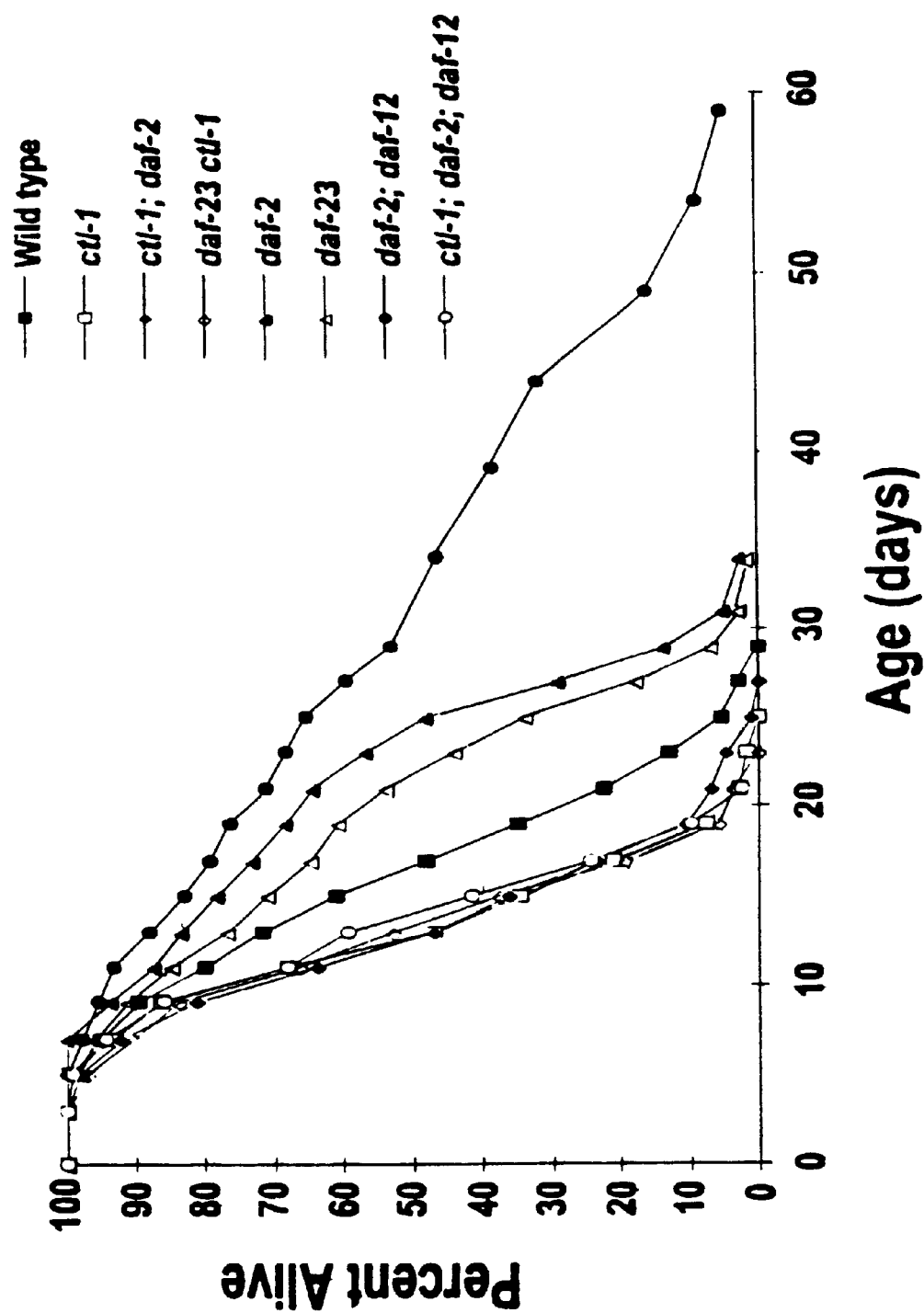
FIG. 6 Effect of ctl-1 activity on lifespan.

The pattern of ctl-2 expression in age-1 animals and their controls were identical: ctl-2 mRNA declined as the animals aged. In contrast, the level of ctl-1 mRNA actually increased to 9 days and remained high 12 days after hatching. The abundance of ctl-1 MRNA seen in daf-2 dauer larvae and in old age-1 animals suggests that ctl-1 is needed for life-span extension of both dauer larvae and age-1 worms. Moreover, these results strongly suggest that ctl-1 and not ctl-2 is a downstream target of daf-2 and age-1 (a.k.a. daf-23).

ctl-1(u800) shortens life-span. Using a subtractive cDNA screen (C. Ma and M. Chalfie, unpub. data), we serendipitously discovered a catalase cDNA whose mRNA was reduced by at least ten fold in the strain TU1061 (data not shown). Since northern blots of mRNA for strains with known mutations in TU1061 did not show this reduction, none of these genes was responsible for the reduction. The defect was identified as a deletion of a single G in the codon 42 (Arg) of ctl-1. This change resulted in a stop codon at codon 51. The ctl-1 mutation was outcrossed from TU1061; it is contained in the TU2463 strain. As expected total catalase activity of the outcrossed mutant animals is reduced by more than 50%, both as first stage (L1) larvae and as adults when compared to wilde-typetype animals (FIG. 5). The mean life-span of the mutant animals is approximately 30% less than that of wilde-typetype animals at 200 (FIG. 6; 50% survival at 13.2 days for the mutants, 17.2 days for wild type). Moreover, dauer survival was similarly reduced by the ctl-1 mutation (data not shown). ctl-1(u800) is epistatic to daf-c mutations that extend life-span. Double and triple mutants containing daf-c mutations and ctl-1(u800) do not show any life-span extension; they live no longer than animals possessing the ctl-1 defect alone. Specifically 50% of daf-2(e1370); daf-12(m25), daf-23 (mg44), and daf-2 (e1370) animals are alive at 34.4, 21.5 and 23.8 days respectively. The life-spans of ctl-1 (u800); daf-2(e1370); daf-12(m25), daf-23(mg44) ctl-1(u800), and ctl-1(u800); daf-2(e1370) animals are 13.5, 13.2, and 12.8 days (FIG. 6). These results suggest that ctl-1(u800) is epistatic to, i.e., downstream of, the genes in the dauer formation pathway.

Experimental Discussion

C. elegans contains two catalases: CTL-2, a typical peroxisomal catalase, and CTL-1, an unusual, cytosolic catalase. The expression of ctl-1 is strongly increased in the dauer larvae, arguing that ctl-1 must play some specific role in the dauer larvae. CTL-1 may act as a general scavenger of hydrogen peroxide in the cytosol, or it may protect cells from the effects of an, as yet unknown, dauer specific metabolic process such as peroxisomal beta-oxidation. Until the metabolic processes occurring in the dauer larvae are defined, the role of CTL-1 in dauer metabolism will be unclear.

ctl-1 is up-regulated in the daf-2 dauer larvae and in the long-lived age-1 mutant, but not in similarly aged wilde-typetype animals. Thus, ctl-1 is a likely downstream target of the daf life-span extension signaling pathway. Because the ctl-1 mutation is epistatic to the long life phenotypes of the daf-2, daf-23, and daf-2; daf-12 mutations, ctl-1 is necessary for the life-span extension seen in these mutants.

C. elegans is the first animal shown to have two different transcripts encoding catalases with different subcellular distributions. Because C. elegans does not have detectable glutathione peroxidase activity, CTL-1 may fulfill the need for a cytosolic hydrogen peroxide scavenger.

We believe that C. elegans utilizes CTL-1 to cope with oxidative stress in the cytosol, where it may work with a superoxide dismutase. Counteracting cytosolic oxidative stress may allow animals to survive long periods of pre-reproductive dormancy in the dauer larvae. The misexpression of the dauer life-span extension program, and particularly CTL-1, in late life appears to cause the life-span extension seen in the long lived mutants.

Many models for the evolution of senescence suggest that a trade-off is made between reproduction and life extension (see, e.g., Kirkwood and Rose, 1991). Arguments such as these suggest that life-span extension genes, often acting after a period of reproduction, would not be selected for. However, the nematode dauer larvae presents an unusual situation in which life-span extension is needed before animals reproduce. Selection for life-span extension genes would, thus, enable the animals to produce progeny.

Yeast (Ruis and Koller, 1997) and plants (Scandalios et al., 1997), each of which have pre-reproductive dormant stages (stationary phase in yeast and the ungerminated seed in plants), also have cytosolic catalases. Although no gene for a cytosolic catalase has been reported, Roels and colleagues (Roels 1976, Roels et al., 1977) histochemically localized catalase activity to the cytosol of sheep, guinea pig, and rhesus monkey hepatocytes. If confirmed, this observation suggests that cytosolic catalases may be widespread. A common observation is that caloric restriction leads to life-span extension. Since cytosolic catalases are expressed in E. coli (Loewen, 1997), yeast, plants, and nematodes during periods of dormancy or starvation, cytosolic catalases (and other enzymes that inactivate reactive oxygen species) may underlie the life-span extension produced by caloric restriction.

Experimental Procedures

Maintenance of Nematode Strains

Animals were grown, unless otherwise noted, at 20° as before (Brenner, 1974; Way and Chalfie, 1988). Mutations used were fer-15(b26ts)II (Ward et al., 1981), age-1 (hx546) II (Klass, 1983), daf-23(mg44)II (Gottlieb and Ruvkun, 1994), ctl-1(u800)II, unc-52(e444)II (Brenner, 1974), daf-2 (e1370)III (Riddle, 1977), daf-12(m25)X (Riddle et al., 1981), and mec-10(u20) (Huang and Chalfie, 1994). The age-1 strain we used, TJ401, also contained the fer-15 mutation; the strain DH26, which contains the fer-15 mutation alone was used as a control. These strains were particularly useful for catalase assays and Northern analysis of staged populations, because the fer-15 mutation conveyed sterility at 25°.

Multiple mutant strains were constructed using standard methods (Brenner, 1974). In these constructions ctl-1 inclusion was generated by the exclusion of the unc-52 mutation. Similarly, daf-12 inclusion was generated by the exclusion of the mec-10 mutation.

Catalase Assays

Animals were harvested at various times from cultures synchronized by hypochlorite treatment (Sulston and Hodgkin, 1988) and washed five times with M9 buffer (Brenner, 1974). Lysates were prepared by grinding animals with 0.5 mm glass beads in 20 mM Tris-HCl (pH 7.5), 50 mM KOAc, 2 mM EDTA, 100 mM sorbitol. Catalase assays were performed as described by Peters et al. (1972). Protein was measured according to Bradford (1976).

Molecular Biology

Unless noted, general molecular biology techniques followed the protocols in Sambrook et al. (1989). The full-length cDNAs corresponding to the ctl-1 and ctl-2 mRNAs were identified by screening a Lambda-Zap CDNA library (Barstead and Waterston, 1989) using the entire expressed sequence tag cm20b12 (Waterston et al., 1992) as a probe. Plaques containing the complete ctl-1 and ctl-2 cDNAs were recovered and pbluescript plasmid were generated following the Lambda-Zap protocols (Stratagene, LaJolla, Calif.). A ctl-1 cDNA plasmid, TU#527 was unidirectionally deleted using the Erase-A-Base system (Promega Corp., Madison, Wis.) and the resulting DNAs were sequenceed using a Prism cycle sequencing kit and an Applied Biosystems model 373 sequencer. A ctl-2 cDNA plasmid, TU#528, was sequenced from the 5' and 3' ends and found to be identical to CECAT, a *C. elegans* cDNA encoding a putative peroxisomal catalase that was deposited in the EMBL database by K. J. Henkle-Duehrsen.

RNA for Northern blots was prepared from synchronous populations of animals grown at 25° C. Dauer larvae were prepared by growing daf-2(e1370) animals at 25° C. Total RNA was prepared (Chirgwin et al., 1979) from animals that were washed 5 times with M9 buffer (Brenner, 1974) to remove bacteria. RNA (5 µg) was electrophoresed through a 1% formaldehyde gel and transferred to nitrocellulose filters (Chomczynski, 1992). Membranes where hybridized (Liu et al., 1996) with ctl-1- or ctl-2- specific [$^{32}$P]-labeled riboprobes (Sambrook et al., 1989) complementary to the 3'-most 264 nucleotides of the ctl-1 open reading frame and 3'-most 380 nucleotides of the ctl-2 open reading frame, respectively.

Identification and Characterization of ctl-1(u800)

In the course of experiments with TU1061, (C. Ma and M. Chalfie, unpub. data), we identified 4 cDNA clones encoding the same cDNA that showed reduced expression when compared to wild type. We sequenced these partial cDNAs, isolated a larger cDNA, and found that it encoded a catalase. The gene for this catalase is named ctl-1. Initial assignment of the ctl-1 cDNA to the yeast artificial chromosome grid of *C. elegans* genomic DNA suggested that the gene was located where another catalase cDNA, cm20b12. was found (this cDNA encodes the ctl-2 catalase). We outcrossed the TU1061 strain based on this map information and obtained a strain that on testing produced animals with a significant reduction in life-span (see RESULTS). Genetic mapping of the effect on life-span placed the mutation in the correct position (i.e., between lin-7 and unc-52) on chromosome II.

To identify the site of the ctl-1(u800) mutation, we obtained RT-PCR amplified cDNA for the entire ctl-1 open reading frame using the Marathon cDNA amplification kit (Clontech, Palo Alto, Calif.). The amplified cDNA was cloned into the pCR2.1 vector (Invitrogen, San Diego, Calif.) and sequenced using a Sequenase 2.0 kit (US Biochemicals, Cleveland, Ohio).

Determination of Life-span

Synchronous populations of worms were placed on 60 mm plates seeded with OP50-1 as two day old larvae (8–12 individuals per plate, 100–150 individuals per experiment) and grown at 20° C. Individuals were moved to fresh plates daily for 9 days after hatching and weekly thereafter. Plates were examined at various times for live, dead and missing individuals (missing animals were not included in the calculation of life-span). Individuals were scored as dead when they became unresponsive to prodding with a wire probe and no pharyngeal pumping could be observed (this inactivity was taken as the measure of death in the animal; see e.g. Larsen et al., 1995).

Construction and Analysis of ctl-gfp Fusions

An XbaI site was placed at the first codon of the ctl-1 and ctl-2 cDNAs by PCR amplification using the sense primer 5'-CGCTCTAGAAACCAAAATGCCAAACGA-3' (SEQ. ID NO. 1) and the antisense primer 5'-CTCGAAGTATCCATGGGCTCCG-3'(SEQ. ID NO. 2). The amplified fragment was cut with XbaI/NcoI and ligated into XbaI/NcoI-cut TU#527 and TU#528 to generate TU#529 and TU#530. The gene for the green fluorescent protein (gfp) was amplified from TU#65 (Chalfie et al., 1994) using the sense primer 5'-GGCGCTAGCAACAAAAATGAGTAAAGGAGAA GAACTTTTTC-3' (SEQ. ID NO. 3)and the antisense primer 5'-GCCTCTAGAATCTGCTTGCTAGCTTTGTATAG-3', (SEQ. ID NO. 4). The amplified fragment was cleaved with XbaI/NheI and ligated into XbaI-cut TU#529 and TU#530 to generate in frame fusions between the gfp and ctl-1 and ctl-2. The fusion was excised with XbaI/HindIII and ligated into XbaI/HindIII-cut pEMBLyex4 (Baldari, 1987) generating the expression plasmids TU#531 and TU#532. These last plasmids were transformed (Ito et al., 1983) into *Saccharomyces cerevisiae* strain FY 834 (Winston et al., 1995). Fusions were expressed by growth at 30° in SC media (Sherman, 1991) containing 0.2% galactose.

Additional experiments are also planned to further confirm that the ctl-1 gene can extend life-span. For the first set of future experiments, we will transform animals as before with a plasmid in which the ctl-1 coding region is expressed from a ubiquitously expressed promoter for a glycolytic enzyme and test life span in a population of animals as before. Because, as in the Drosophila experiments, catalase overexpression may have to be matched with that of SOD, we will also perform experiments in which we cotransform the animals with a similar sod-1 containing plasmid containing an identical promoter, thereby promoting the expression of the *C. Elegans* sod-1 gene. At least one control will contain similar constructs containing the ctl-2 gene in place of the ctl-1 gene.

In addition to the first set of future experiments, we also plan to perform experiments showing that CTL-2 lacking the C-terminal peroxisomal localization signal is localized to the cytosol and this change results in an extension of life-span. Such experiments may be performed by transforming animals with a plasmid containing a ctl-2 gene which has been modified to lack region encoding the C-terminal peroxisomal localization signal References Amstad, P., Peskin, A., Shah, G., Mirault, M. -E., Moret, R., Zbinden, I., and Cerutti, P. (1991) The balance between Cu, Zn-superoxide dismutase and catalase affects the sensitivity of mouse epidermal cells to oxidative stress. *Biochem.* 30: 9305–9313.

Anderson, G. L. (1982) Superoxide dismutase activity in dauerlarvae of Caenorhabditis elegans (Nematoda: Rhabditidae) *Can. J. Zool.* 60: 288–291.

Baldari, C., Murray, J. A. H., Ghiara, P., Cesareni, G., and Galeotti, C. L. (1987) A novel leader peptide which allows efficient secretion of a fragment of human interleukin Iβ in *Saccharomyces cerevisiae. EMBO J.* 6: 229–234.

Barstead, R., and Waterston, R. (1989) The basal component of the nematode dense-body is vinculin. *J. Biol. Chem.* 264: 10177–10185.

Bradford, M. M. (1976) A rapid and sensitive method for the quantitation of microgram quantities of proteins utilizing the principle of protein dye binding. *Anal. Biochem.* 72: 248–254.

Brenner, S. (1974) The genetics of *Caenorhabditis elegans. Genetics* 77: 71–93.

Chalfie, M., Tu, Y., Euskirchen, G., Ward, W. W., and Prasher, D. C. (1994) Green fluorescent protein as a marker for gene expression. *Science,* 263: 802–805.

Chirgwin, J. M., Przybyla, A. E., MacDonald, R. J., and Rutter, W. J. (1979) Isolation of biologically active ribonucleic acid from sources enriched in ribonuclease. *Biochem.* 18: 5294–5299.

Chomczynski, P. (1992) One-hour alkaline capillary transfer for blotting DNA and RNA. *Anal. Biochem.* 201: 134–139.

Coulson, A., Huynh C., Kozono, Y., and Shownkeen, R. (1995) The physical map of *Caenorhabditis elegans* genome. In *Caenorhabditis elegans: Modern Biological Analysis of an Organism.* H. F. Epstein and D. C. Shakes (eds.) *Meth. Cell Biol.* vol. 48, Academic Press, pp. 533–550.

Friedman, D. B., and Johnson, T. E. (1987) A mutation in the age-1 gene in *Caenorhabditis elegans* lengthens life and reduces hermaphrodite fertility. *Genetics* 118: 75–86.

Gerschman, R., Gilbert, D. L., Nye, S., Dwyer, P., and Fenn, W. O. (1954) Oxygen poisoning and x-irradiation: A mechanism in common. *Science* 119: 623–629.

Gottlieb, S., and Ruvkun, G. (1994) daf-2, daf-16, and daf-23: Genetically interacting genes controlling dauer formation in *Caenorhabditis elegans.* *Genetics* 137: 107–120.

Gould, S. J., Keller, G. -A., Hosken, N., Wilkinson, J., and Subramani, S. (1989) A conserved tripeptide sorts proteins to peroxisomes. *J. Cell Biol.* 108: 1657–1664.

Harman, D. (1956) Aging: A theory based on free radical and radiation biology. *J. Gerontol.* 11: 298–300.

Huang, M., and Chalfie, M. (1994) Gene interactions affecting mechanosensory transduction in *Caenorhabditis elegans.* *Nature,* 367: 467–470.

Ito, H., Fukuda, Y., Kousaku, M., and Kimura, A. (1983) Transformation of intact yeast cells treated with alkali cations. *J. Bacteriol.* 153: 163–168.

Kenyon, C., Chang, J., Gensch, E., Rudner, A., and Tabtiang, R. (1993) A *C. elegans* mutant that lives twice as long as wild type. *Nature* 366: 461–464.

Kirkwood, T. B. L., and Rose, M. R. (1991) Evolution of senescence: late survival sacrificed for reproduction. *Phil. Trans. R. Soc. Lond. B* 332: 15–24.

Klass, M. R. (1983) A method for the isolation of longevity mutants in the nematode *Caenorhabditis elegans* and initial results. *Mech. Ageing Dev.* 22: 279–286.

Klass, M., and Hirsh, D. (1976) Non-aging developmental variant of *Caenorhabditis elegans.* *Nature* 260: 523–525.

Larsen, P. (1993) Aging and resistance to oxidative damage in *Caenorhabditis elegans.* *Proc. Natl. Acad. Sci. USA* 90: 8905–8909.

Larsen, P., Albert, P. S., and Riddle, D. L. (1995) Genes that regulate both development and longevity in *Caenorhabditis elegans.* *Genetics* 139: 1567–1583.

Liu, Z., Taub, C. C., and McClung, C. R. (1996) Identification of an *Arabidopsis thaliana* ribulose-1,5-bisphosphate carboxylase/oxygenase activase (RCA) minimal promoter regulated by light and the circadian clock. *Plant Physiol.* 112: 43–51.

Loewen, P. (1997) Bacterial catalases. in *Oxidative Stress and the Molecular Biology of Antioxidant Defenses.* J. G. Scandalios (ed.), Cold Spring Harbor Press, Cold Spring Harbor, N.Y. pp. 273–308.

Malone, E. A., Inoue, T., Thomas, J. H. (1996) Genetic analysis of the roles of daf-28 and age-1 in regulating *Caenorhabditis elegans* dauer formation. *Genetics* 143: 1193–1205.

Morris, J. Z., Tissenbaum, H. A., Ruvkun, G. (1996) A phosphatidylinositol-3-OH kinase family member regulating longevity and diapause in *Caenorhabditis elegans.* *Nature* 382: 536–539.

Orr, W. C. and Sohal, R. S. (1992) The effects of catalase gene overexpression on life span and resistance to oxidative stress in transgenic *Drosophila melanogaster.* *Arch. Biochem. Biophys.* 297: 35–41.

Orr, W. C. and Sohal, R. S. (1993) Effects of Cu—Zn superoxide dismutase overexpression on life span and resistance ot oxidative stress in transgenic *Drosophila melanogaster. Arch. Biochem. Biophys.* 301: 34–40.

Orr, W. C. and Sohal, R. S. (1994) Extension of life-span by overexpression of superoxide dismutase and catalase in *Drosophila melanogaster. Science* 263: 1128–1130.

Peters, T. J., Muller, M., and DeDuve, C. (1972) Lysosomes of the arterial wall. I. Isolation and subcellular fractionation of cells from normal rabbit aorta. *J. Exper. Med.* 136: 1117–1139.

Phillips, J. P., Campbell, S. D., Michaud, D., Charbonneau, M. and Hilliker, A. J. (1989) Null mutation of copper/zinc superoxide dismutase in Drosophila confers hypersensitivity to paraquat and reduced longevity. *Proc. Natl. Acad. Sci. USA* 86: 2761–2765.

Riddle, D. L. (1977) A genetic pathway for dauer larva formation in *C. elegans. Stadler Genetics Symposium* 9: 101–120.

Riddle, D. L., Swanson, M. M., and Albert, P. S. (1981) Interacting genes in nematode dauer larva formation. *Nature* 290: 668–671

Roberts, L. S., and Janovy, Jr., J. (1996) *Gerald D. Schmitt and Larry S. Roberts Foundations of Parasitology,* Wm. C. Brown, Dubuque, Id.

Roels, F. (1976) Cytochemical demonstration of extraperoxisomal catalase. I. Sheep liver. *J. Histochem. Cytochem.* 24: 713–724.

Roels, F., de Coster W., and Goldfischer, S. (1977) Cytochemical demonstration of extraperoxisomal catalase. II. Liver of rhesus monkey and guinea pig. *J. Histochem. Cytochem.* 25: 157–160.

Ruis, H., and Koller, F. (1997) Biochemistry, molecular biology, and cell biology of yeast and fungal catalases. in *Oxidative Stress and the Molecular Biology of Antioxidant Defenses.* J. G. Scandalios (ed.), Cold Spring Harbor Press, Cold Spring Harbor, N.Y. pp. 309–342

Sambrook, J., Fritsch, E. F., and Maniatis, T. (1989) *Molecular Cloning: A Laboratory Manual, $2^{nd}$* ed., Cold Spring Harbor Laboratory Press, Cold Spring Harbor, N.Y.

Scandalios, J. G., Guan, L., and Polidoros, A. N. (1997) Catalases in plants: Gene structure, properties, regulation, and expression. in *Oxidative Stress and the Molecular Biology of Antioxidant Defenses.* J. G. Scandalios (ed.), Cold Spring Harbor Press, Cold Spring Harbor, N.Y. pp. 343–406.

Seta, N. O.L., Hayashi, S., and Tenner, G. M. (1990) Overexpression of Cu—Zn superoxide dismutase in Drosophila does not affect life-span. *Proc. Natl. Acad. Sci. USA* 87: 4270–4274.

Sherman, F. (1991) Getting started with yeast. *Meth. Enzymol.* 194: 3–20.

Sohal, R. S. and Allen, R. G. (1990) Oxidative stress as a causal factor in differentiation and aging: a unifying hypothesis. *Exp. Gerontol.* 25: 499–522.

Staveley, B. E., Phillips, J. P. and Hilliker, A. J. (1990) Phenotypic consequences of copper-zinc superoxide dismutase overexpression in *Drosophila melanogaster. Genome* 33: 867–872.

Sulston, J., and Hodgkin, J. (1988) Methods. in *The Nematode Caenorhabditis elegans.* W. B. Wood (ed.) pp. 587–606.

Thomas, J. H., Birnby, D. A., and Vowels, J. J. (1993) Evidence for parallel processing of sensory information controlling dauer formation in *Caenorhabditis elegans*. *Genetics* 134: 1105–1117.

Vanfleteren, J. R. (1993) Oxidative stress and ageing in *Caenorhabditis elegans. Biochem. J.* 292: 605–608.

Vowells, J. J., and Thomas, J. H. (1992) Genetic analysis of chemosensory control of dauer formation in *Caenorhabditis elegans. Genetics* 130: 105–123.

Ward, S., Argon, Y., and Nelson, G. A. (1981) Sperm morphogenesis in wilde-typetype and fertilization defective mutants of *Caenorhabditis elegans. J. Cell Biol.* 81: 26–44.

Waterston, R., Martin, C., Craxton, M., Huynh, C., Coulson, A., Hilier, L. Durbin, R., Green, P., Shown-keen, R., Halloran, N., Metzstein, M., Hawkins, T., Wilson, R., Berks, M., Du, Z., Thomas, K. Thierry-Mieg, J., and Sulston, J. (1992) *Nature Genetics* 1: 114–123.

Way, J. C., and Chalfie, M. (1988) mec-3, a homeobox-containing gene that specifies differentiation of the touch receptor neurons in *Caenorhabditis elegans. Cell* 54: 5–16.

Winston, F., Dollard, C., and Ricupero-Hovasse, S. L. (1995) Construction of a set of convenient *Saccharomyces cerevisiae* strains that are isogenic to S288C. *Yeast* 11: 53–55.

---

What is claimed is:

1. An isolated nucleic acid molecule encoding a ctl-1 cytosolic catalase.

2. The isolated nucleic acid molecule of claim 1, wherein the nucleic acid molecule is a DNA molecule.

3. The isolated nucleic acid molecule of claim 2, wherein the nucleic acid molecule is a cDNA molecule or a genomic DNA molecule.

4. The isolated cDNA molecule of claim 3, wherein the nucleotide sequence is set forth in FIG. 7 (SEQ. ID No:7).

5. The genomic DNA molecule of claim 3, wherein the ctl-1 cytosolic catalase-encoding nucleotide sequence is shown in FIG. 8A (SEQ. ID NO:8).

6. The isolated nucleic acid molecule of claim 1, wherein the nucleic acid molecule is an RNA molecule.

7. The isolated nucleic acid molecule of claim 1, wherein the ctl-1 cytosolic catalase has the amino acid sequence shown in FIG. 3 (SEQ. ID NO:5).

8. A vector comprising a nucleic acid sequence encoding a ctl-1 cytosolic catalase.

9. The vector of claim 8, wherein the vector is a plasmid.

10. A host vector system for the production of a ctl-1 cytosolic catalase comprising the vector of claim 8 in a suitable host.

11. The host vector system of claim 10, wherein the suitable host is a bacterial cell, yeast cell, insect cell, animal cell, or plant cell.

12. The plasmid of claim 9, designated TU#527 (ATCC Accession No. 209503).

13. A cell comprising an exogenous nucleic acid molecule encoding a ctl-1 cytosolic catalase.

14. A cell comprising the vector of claim 8.

15. A composition comprising (a) a nucleic acid molecule comprising a ctl-1 cytosolic catalase-encoding sequence which, when introduced into a cell, causes the expression of an amount of the ctl-1 cytosolic catalase sufficient to increase the life-span of the cell, and (b) a suitable carrier.

16. The composition of claim 15, further comprising a nucleic acid molecule comprising a superoxide dismutase-encoding sequence, which molecule may be the same or different than the molecule comprising the ctl-1 cytosolic catalase-encoding sequence.

* * * * *